United States Patent
Cho et al.

(10) Patent No.: US 11,330,999 B2
(45) Date of Patent: May 17, 2022

(54) HYPERPOLARIZED AND DEUTERIUM EXCHANGED HYPERPOLARIZED $^{13}$C AND $^{15}$N-LABELED XANTHINE, ARGININE, GLUTAMINE, AND UREA PROBES

(71) Applicant: MEMORIAL SLOAN KETTERING CANCER CENTER, New York, NY (US)

(72) Inventors: Andrew Cho, New York, NY (US); Roozbeh Eskandari, New York, NY (US); Valentina Di Gialleonardo, New York, NY (US); Kayvan R. Keshari, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 0 days.

(21) Appl. No.: 16/646,549

(22) PCT Filed: Sep. 10, 2018

(86) PCT No.: PCT/US2018/050307
§ 371 (c)(1),
(2) Date: Mar. 11, 2020

(87) PCT Pub. No.: WO2019/055358
PCT Pub. Date: Mar. 21, 2019

(65) Prior Publication Data
US 2020/0260983 A1    Aug. 20, 2020

Related U.S. Application Data

(60) Provisional application No. 62/679,501, filed on Jun. 1, 2018, provisional application No. 62/557,696, filed on Sep. 12, 2017.

(51) Int. Cl.
*A61B 5/055*    (2006.01)
*C07B 59/00*    (2006.01)
(Continued)

(52) U.S. Cl.
CPC .............. *A61B 5/055* (2013.01); *C07B 59/00* (2013.01); *C07C 237/06* (2013.01);
(Continued)

(58) Field of Classification Search
CPC ..... A61B 5/055; C07C 279/14; C07C 237/06; C07D 473/06; C07B 59/00; C07B 2200/05; A61K 49/10
See application file for complete search history.

(56) References Cited

U.S. PATENT DOCUMENTS 6,466,814 B1 * 10/2002 Ardenkjaer-Larsen ...................... A61K 49/10
600/420
2013/0149250 A1    6/2013 Wilson et al.

OTHER PUBLICATIONS

Alsabati, Neoplasma, 1980, 27(1), p. 95-9 (abstract). (Year: 1980).*
(Continued)

*Primary Examiner* — Michael G. Hartley
*Assistant Examiner* — Leah H Schlientz
(74) *Attorney, Agent, or Firm* — Foley & Lardner LLP

(57) ABSTRACT

The present technology provides $^{13}$C- and $^{15}$N-labeled probes for imaging one or more mammalian cells using magnetic resonance. Thus, $^{13}$C- and $^{15}$N-labeled arginine (compound of formula I), xanthine (compounds of formula II and formula III), urea (compounds of formula IV), and glutamine (compounds of formula V), stereoisomers, tautomers, and pharmaceutically acceptable salts thereof are provided. Further methods of making the labelled probes and methods of using the probes to detect arginase, xanthine oxidase, and glutaminase metabolites and activity are provided.

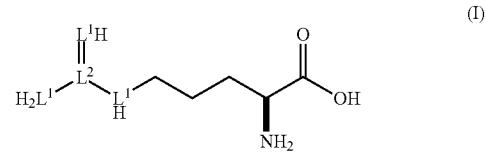

(I)

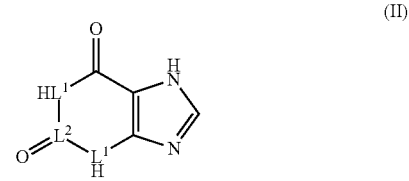

(II)

(III)

(IV)

(V)

(Continued)

19 Claims, 12 Drawing Sheets

(51) Int. Cl.
 C07C 237/06 (2006.01)
 C07C 279/14 (2006.01)
 C07D 473/06 (2006.01)
 A61K 49/10 (2006.01)
(52) U.S. Cl.
 CPC .......... *C07C 279/14* (2013.01); *C07D 473/06* (2013.01); *A61K 49/10* (2013.01); *C07B 2200/05* (2013.01)

(56) References Cited

OTHER PUBLICATIONS

Chiavazza et al., "Earth's magnetic field enabled scalar coupling relaxation of 13C nuclei bound to fast-relaxing quadrupolar 14N in amide groups," Journal of Magnetic Resonance, vol. 227 (Feb. 2013).

Cho et al., Noninvasive Interrogation of Cancer Metabolism with Hyperpolarized 13C MRI, Journal of Nuclear Medicine, vol. 58, No. 8, pp. 1201-1206 (Jun. 8, 2017).

International Search Report and Written Opinion, PCT/US2018/050307, Memorial Sloan Kettering Cancer Center (dated Nov. 14, 2018).

Pubchem, Compound Summary for SID 313056700, retrieved from: https://pubchem.ncbi.nlm.nih.gov/substance/313056700 (Apr. 28, 2016).

Najac Chloe et al: "Detection of inflammatory cell function using 13C magnetic resonance spectroscopy of hyperpolarized [6-13C]-arginine", Scientific Reports, vol. 6, No. 1, Aug. 10, 2016 (Aug. 10, 2016).

Yamaguchi Koya et al: "In situ analysis of [8-13C-7-15N]-double-labelled theophylline by a triple resonance NMR technique", Analytical Methods, vol. 3, No. 7, Jan. 1, 2011 (Jan. 1, 2011), p. 1664, XP55790386, GBR.

A. Cho, et al., "A Non-synthetic Approach to Extending the Lifetime of Hyperpolarized Molecules using D2O Solvation," J. Magn. Reson. 295, pp. 57-62 (2018).

\* cited by examiner

Expression level of Xanthine Transporter and Oxidase

HYPERPOLARIZED AND DEUTERIUM EXCHANGED HYPERPOLARIZED $^{13}$C AND $^{15}$N-LABELED XANTHINE, ARGININE, GLUTAMINE, AND UREA PROBES

CROSS-REFERENCE TO RELATED APPLICATIONS

The present application is a U.S. National Phase Application under 35 U.S.C. § 371 of International Application No. PCT/US2018/050307, filed Sep. 10, 2018, which claims the benefit of and priority to U.S. Provisional Application No. 62/557,696, filed Sep. 12, 2017, and U.S. Provisional Patent Application No. 62/679,501, filed Jun. 1, 2018, the entire contents of which are incorporated herein by reference.

FIELD

The present technology is directed to compounds, compositions, and methods related to $^{13}$C and $^{15}$N labeled probes for use in in vitro and in vivo imaging. In particular, the present compounds are $^{13}$C and $^{15}$N labeled xanthine, arginine, glutamine, and urea, as well as deuterium exchanged analogs thereof.

SUMMARY

Disclosed herein, in one aspect of the present technology, a compound according to formula I

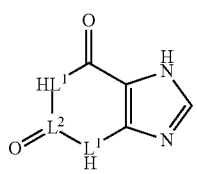
(I)

stereoisomers, tautomers, and/or pharmaceutically acceptable salts thereof; wherein $L^1$ is $^{15}$N, $L^2$ is $^{13}$C, and ▬▬ is a member selected from the group consisting of ⋯⋯⦀⦀⦀, ▬▬◤, and a mixture thereof.

In another aspect, disclosed herein, a compound according to formula II

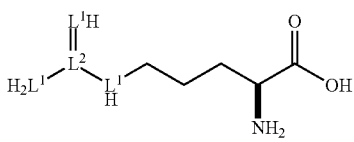
(II)

tautomers, and/or pharmaceutically acceptable salts thereof; wherein $L^1$ is $^{15}$N and $L^2$ is $^{13}$C.

In yet another aspect, disclosed herein, a compound according to formula III

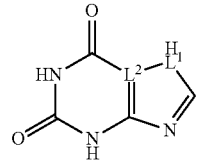
(III)

tautomers, and/or pharmaceutically acceptable salts thereof; wherein $L^1$ is $^{15}$N and $L^2$ is $^{13}$C.

In an aspect of the present technology, a pharmaceutical composition is provided that includes any of the compounds of formula I, formula II, or formula III or any other aspect or embodiment described herein and a pharmaceutically acceptable carrier.

In a related aspect, the present technology provides a method of preparing a compound of formula I as described herein in any embodiment, including reacting a compound of formula IA with a compound of formula IB:

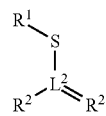
(IA)

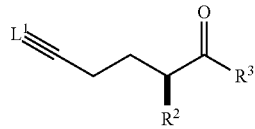
(IB)

wherein: $R^1$ is a C1-C3 alkyl, $R^2$ is a protected or unprotected $^{15}$N group, $R^3$ is a protected or unprotected —OH, $L^1$ is $^{15}$N, $L^2$ is $^{13}$C, and ▬▬ is a member selected from the group including ⋯⋯⦀⦀⦀, ▬▬◤, and a mixture thereof.

In another aspect, the present technology provides a method of preparing a compound of formula II, as disclosed herein in any embodiment, including reacting a compound of formula IIA with formamide;

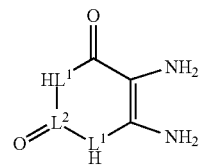
(IIA)

wherein $L^1$ is $^{15}$N and $L^2$ is $^{13}$C.

In another aspect, the present technology provides a method of preparing a compound of formula III, as disclosed herein in any embodiment, including reacting a compound of formula IIIA with formamide;

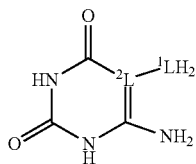

(IIIA)

wherein $L^1$ is $^{15}N$ and $L^2$ is $^{13}C$.

In a further related aspect of the present technology, there is provided a method of imaging that includes administering an effective amount of a composition that includes a hyperpolarized probe to one or more mammalian cells; detecting by magnetic resonance the hyperpolarized probe and/or a metabolite of the probe in the one or more mammalian cells; wherein the hyperpolarized probe is a compound that has been subjected to hyperpolarization and is a compound of formula I, a stereoisomer thereof, a compound of formula II, a compound of formula III, a tautomer and/or a pharmaceutically acceptable salt of any of the foregoing compounds or embodiments thereof as described herein.

In another related aspect of the present technology, there is provided a method of imaging that includes contacting one or more mammalian cells with an effective amount of a composition comprising a deuterium exchanged-hyperpolarized probe to one or more mammalian cells; and detecting (and optionally quantifying) by magnetic resonance the hyperpolarized probe and/or a metabolite of the probe in the one or more mammalian cells; wherein the deuterium exchanged-hyperpolarized probe is a deuterated compound of formula I, and/or stereoisomers thereof, and/or tautomers thereof, and/or pharmaceutically acceptable salts thereof, a deuterated compound of formula IV

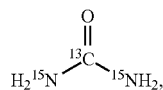

(IV)

and/or tautomers thereof, or a deuterated compound of formula V

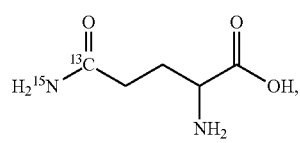

(V)

and/or stereoisomers thereof, and/or tautomers thereof, and/or pharmaceutically acceptable salts thereof; and the deuterated compound has been subjected to hyper polarization. In some embodiments, the deuterated compound exhibits a longer $T_1$ and $T_2$ relaxation time for a $^{13}C$-labeled carbon of a compound of formula I, a stereoisomer thereof, formula V, a stereoisomer thereof, or formula IV, and/or tautomers, and/or pharmaceutically acceptable salts thereof.

In another related aspect of the present technology, there are provided deuterium exchanged-hyperpolarized probes that include a compound of formula VI

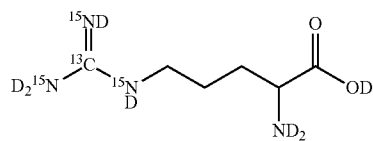

(VI)

or a compound of formula VII

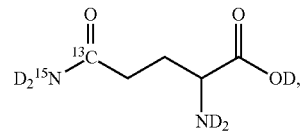

(VII)

stereoisomers, tautomers, and/or pharmaceutically acceptable salts thereof.

BRIEF DESCRIPTION OF THE DRAWINGS

FIG. 5A shows the $^{13}C$ NMR spectrum of the guanidine carbon for [6-$^{13}C$, 6-$^{15}N_3$]-Arginine-HCl (1) and its urea metabolites from arginase-1 (urea, 2) and iNOS (citrulline, 5). FIG. 5B shows the $^{13}C$ NMR spectra of unlabeled and [6-$^{13}C$, 6-$^{15}N_3$]-L-Arginine-HCl (Compound 21) showing the guanidine-carbon peak. FIG. 5C shows the dynamic $^{13}C$ NMR spectra (1T) for [6-$^{13}C$]-arginine and Compound 21 from a single scan using 30° flip angle and 3 s repetition time.

FIG. 9A shows the axial $^1H$ $T_1$-weighted gradient echo of a healthy female Balb/c mouse, with mouse kidneys and 6M $^{13}$C-urea phantom labeled. FIG. 9B shows the signal intensity at each time point throughout entire EPI sequence was summed for each voxel. Images are from the same mouse and have the same field of view as panel A and scaled to the same signal intensity range. FIG. 9C shows the total $^{13}$C signal in the entire field of view at each time point following injection with hyperpolarized urea dissolved in H$_2$O or D$_2$O.

DETAILED DESCRIPTION

Figure 1:
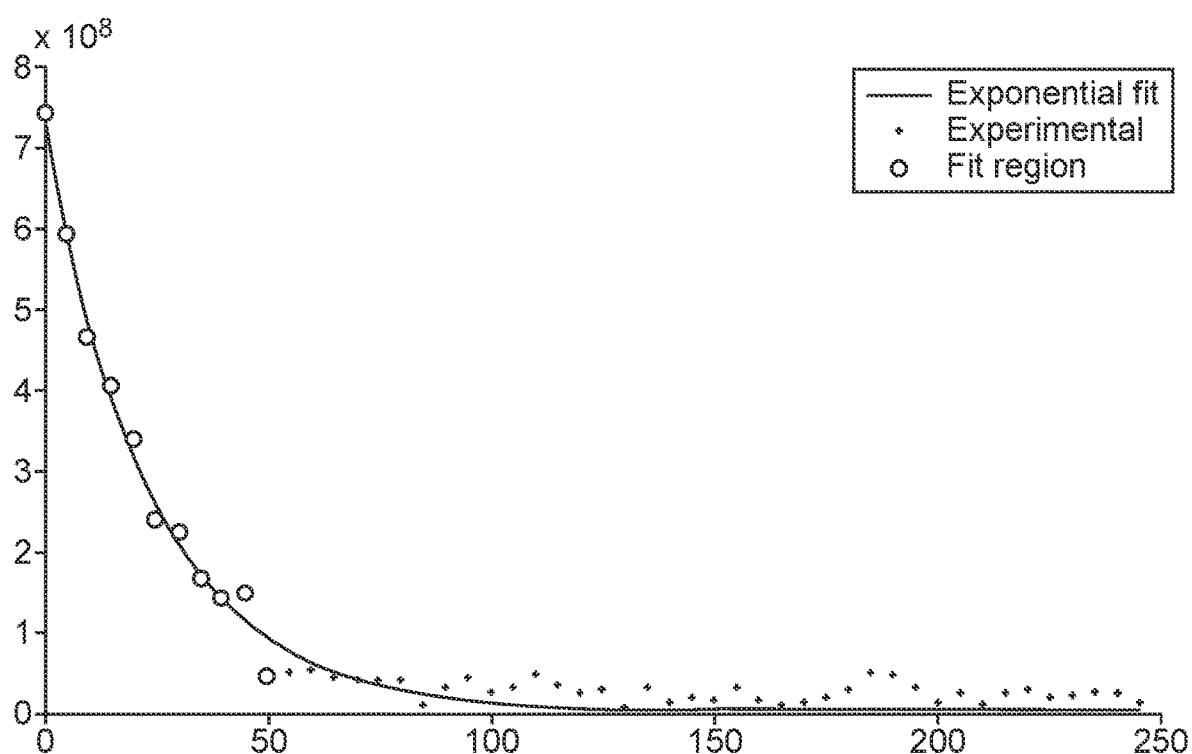
FIG. 1 shows the mono-exponential decay function of hyperpolarized [2-$^{13}C$, 1,3-$^{15}N_2$]-3,7-dihydro-1H-purine-2, 6-dione (Compound 6) to determine spin-lattice relaxation time.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

In various aspects, the present technology provides compounds and methods of imaging using a hyperpolarized probe. The compounds provided herein can be formulated into pharmaceutical compositions that are useful in the disclosed methods. Also provided is the use of the compounds as hyperpolarized probes.

The following terms are used throughout as defined below.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Alkyl groups include straight chain and branched alkyl groups (saturated acyclic hydrocarbons) having from 1 to 12 carbon atoms unless otherwise specified. In some embodiments, alkyl groups have from 1 to 10, from 1 to 8, 1 to 6, or 1 to 3 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neo-pentyl, isopentyl, and 2,2-dimethylpropyl groups.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., Na$^+$, Li$^+$, K$^+$, Ca$^{2+}$, Mg$^{2+}$, Zn$^2$), ammonia or organic amines (e.g., dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, guanidines may exhibit the following isomeric forms in protic organic solution, also referred to as tautomers of each other:

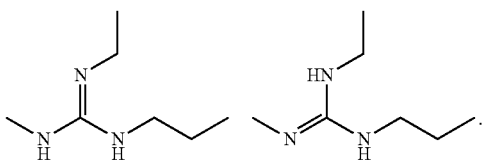

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The terms "cancer" and "tumor," used interchangeably herein, refer to cells or tissues that exhibit an aberrant growth phenotype characterized by a significant loss of control of cell proliferation. The methods and compositions of this disclosure apply to malignant, pre-metastatic, metastatic, and non-metastatic cells.

The present technology provides $^{13}C$ and $^{15}N$ labeled xanthine and arginine compounds. In one aspect, the present technology provides a compound according to formula I

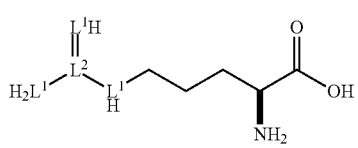

stereoisomers, tautomers, and/or pharmaceutically acceptable salts thereof; wherein $L^1$ is $^{15}N$, $L^2$ is $^{13}C$, and ▬▬▬ is a member selected from the group consisting of ⁙⁞⁞⁞⁞, ◀▬▬ , or a mixture thereof. In some embodiments, the member ▬▬▬ is ◀▬▬. In other embodiments, the member ▬▬▬ is a mixture of ⁙⁞⁞⁞⁞ and ◀▬▬ , e.g., a racemic mixture. In certain embodiments, the compound of formula I, stereoisomer, and/or tautomers thereof is a pharmaceutically acceptable salt, e.g., a HCl salt.

In another aspect, there are provided compounds according to formula II

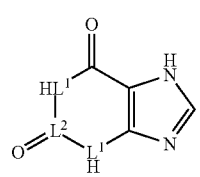

tautomers and/or pharmaceutically acceptable salts thereof; wherein $L^1$ is $^{15}N$ and $L^2$ is $^{13}C$. In certain embodiments, the compound of formula II, and/or tautomers thereof is a pharmaceutically acceptable salt, e.g., a HCl salt.

In yet another aspect, there are provided compounds according to formula III

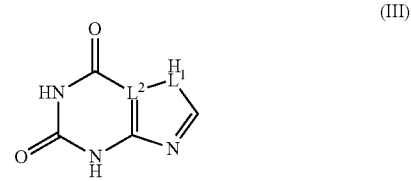

tautomers and/or pharmaceutically acceptable salts thereof; wherein $L^1$ is $^{15}N$ and $L^2$ is $^{13}C$. In certain embodiments, the compound of formula III, and/or tautomers thereof is a pharmaceutically acceptable salt, e.g., a HCl salt.

In an aspect of the present technology, a pharmaceutical composition is provided that includes any of the compounds of formula I, formula II, or formula III or any other aspect or embodiment described herein and a pharmaceutically acceptable carrier. In some embodiments, the pharmaceutical compositions are provided which include an effective amount of a compound of formula I, formula II, formula III or any other aspect or embodiment described herein as hyperpolarized probes in methods of imaging. Such compositions include an effective amount (for the purpose of imaging one or more mammalian cells by magnetic resonance or for therapeutic purposes) of any compound as described herein, including but not limited to a compound of formula I and stereoisomers thereof, formula II, or formula III or any aspects or embodiments of compounds described herein. The pharmaceutical composition may be packaged in unit dosage form.

The pharmaceutical compositions may be prepared by mixing one or more compounds of formula I and stereoisomers thereof, formula II, or formula III, tautomers, and/or pharmaceutical salts or any aspects or embodiments of compounds described herein, with pharmaceutically acceptable carriers, excipients, binders, diluents or the like for use as a hyperpolarized probe. Pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

In an aspect of the present technology, a method of preparing the compounds of formula I or stereoisomers thereof, formula II, and formula III, or tautomers, or pharmaceutically acceptable salts of any aspect or any embodiment is provided. Compounds of formula I, formula II, and formula III are readily synthesized from simple starting materials as shown in Schemes 1-3 and exemplified in the Examples.

As shown in Scheme 1, a compound of formula I, as described herein in any embodiment, may be prepared by reacting a compound of formula IA:

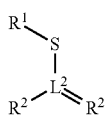

with a compound of formula IB:

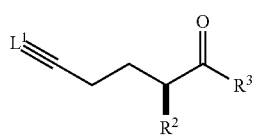

wherein: $R^1$ is a C1-C3 alkyl, $R^2$ is a protected or unprotected $^{15}N$ group, $R^3$ is a protected or unprotected —OH, $L^1$ is $^{15}N$, $L^2$ is $^{13}C$, and ▬▬▬ is a member selected from the group including ⫶⫶⫶⫶⫶⫶, ▬▬▬, or a mixture thereof.

Scheme 1

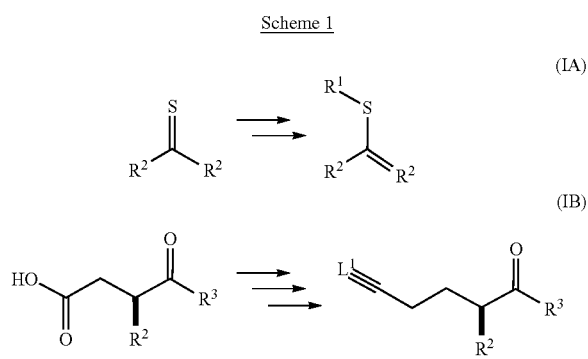

In some embodiments, the compound of formula IA is prepared by reacting [$^{13}C$, $^{15}N_2$]-thiourea with a C1-C3 alkylating agent and base. Suitable alkylating agents include, but are not limited to, methyliodide. In some embodiments, the method includes a compound of formula IA where $R^1$ is methyl. In some embodiments, $R^2$ is a protected $^{15}N$ group. Suitable $^{15}N$ amine protecting groups include, but are not limited to groups which form carbamates with amine and imine nitrogens, such as t-butyloxycarbonyl (Boc), benzyloxycarbonyl (Z), trichloroethyloxy carbonyl, and trimethylsilylethyloxycarbonyl; amides of the nitrogen such as, formamide, acetamide, trifluoroacetamide, and benzamide; sulfonamides of the nitrogen, such as p-toluenesulfonyl; imides of the nitrogen, such as phthalimide, and dithiosuccinimide; and others. In another embodiment, $R^2$ is an unprotected $^{15}N$ group.

In some embodiments, $R^3$ is a protected —OH. Suitable —OH protecting groups include, but are not limited to, alkyl ethers, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate.

The preparation of the compound of formula I may include reacting a compound of formula IA and formula IB in the presence of a catalyst. In some embodiments, the catalyst is a transition metal catalyst, e.g., a palladium catalyst.

As shown in Scheme 2, a compound of formula II, as disclosed herein in any embodiment, may be prepared from a method including reacting the compound of formula IIA with formamide;

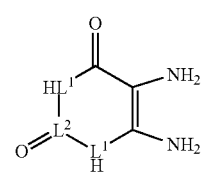

wherein $L^1$ is $^{15}N$ and $L^2$ is $^{13}C$.

Scheme 2

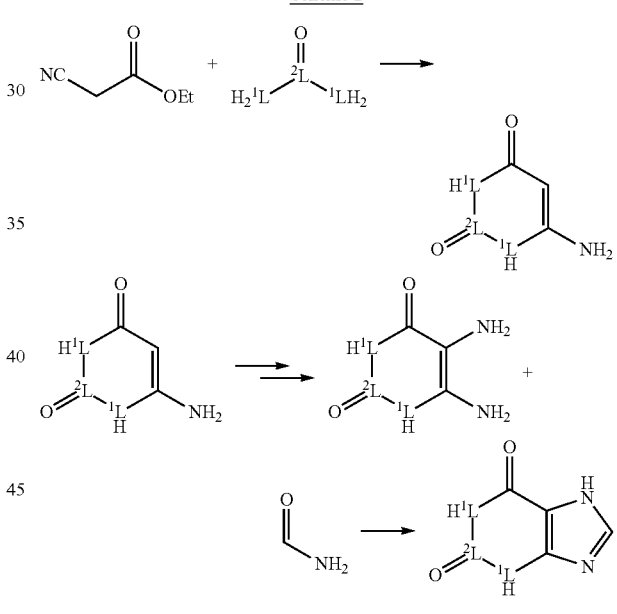

In some embodiments, the reacting occurs at a temperature of about 150° C. to about 200° C. Suitable temperatures include, but are not limited to, from about 150° C., about 160° C. about 170° C., about 180° C., about 190° C., about 200° C. or a range between and including any two of the foregoing values.

In some embodiments, the reacting occurs over a period of about 30 min to about 120 min. Suitable reaction periods include, but are not limited to, about 30 min to about 120 min, about 50 min to about 100 min, or about 60 min to about 90 min. In certain embodiments, the reaction period is from about 60 min to about 90 min.

As shown in Scheme 3, a compound of formula III, as disclosed herein in any embodiment, may be prepared from a method including reacting the compound of formula IIIA with formamide;

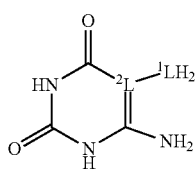

(IIIA)

wherein $L^1$ is $^{15}N$ and $L^2$ is $^{13}C$.

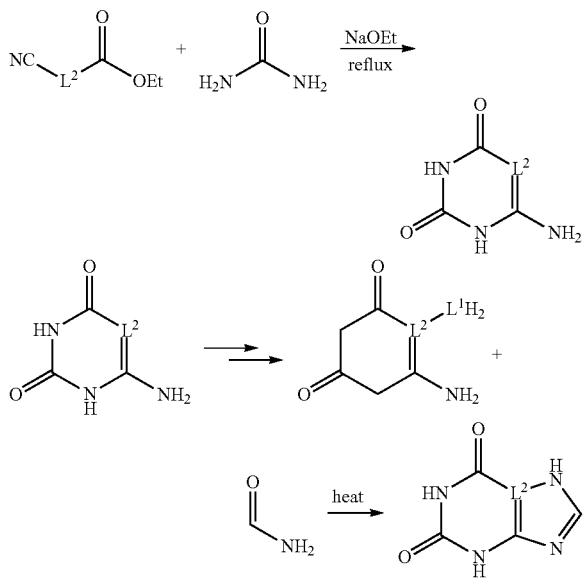

Scheme 3

In some embodiments, the reacting occurs at a temperature of about 150° C. to about 200° C. Suitable temperatures include, but are not limited to, from about 150° C. to about 200° C., about 160° C. to about 200° C., about 170° C. to about 190° C., or about 180° C. to about 190° C. In certain embodiments, the temperature is from 180° C. to about ° C.

In some embodiments, the reacting occurs over a period of about 30 min to about 120 min. Suitable reaction periods include, but are not limited to, about 30 min to about 120 min, about 50 min to about 100 min, or about 60 min to about 90 min. In certain embodiments, the reaction period is from about 60 min to about 90 min.

In a further related aspect, the present technology provides methods of identifying a target of interest including contacting the target of interest with a detectable or imaging effective quantity of a compound of the present technology. In some embodiments, a method of imaging is provided that includes administering an effective amount of a composition that includes a hyperpolarized probe to one or more mammalian cells; detecting (and optionally quantifying) by magnetic resonance the hyperpolarized probe and/or a metabolite of the probe in the one or more mammalian cells; wherein the hyperpolarized probe is a compound that has been subjected to hyperpolarization and is selected from a compound of formula I, a stereoisomer thereof, a compound of formula II, a compound of formula III, and/or a tautomer, and/or a pharmaceutically acceptable salt of any of the foregoing or other compounds described herein.

Figure 5A:
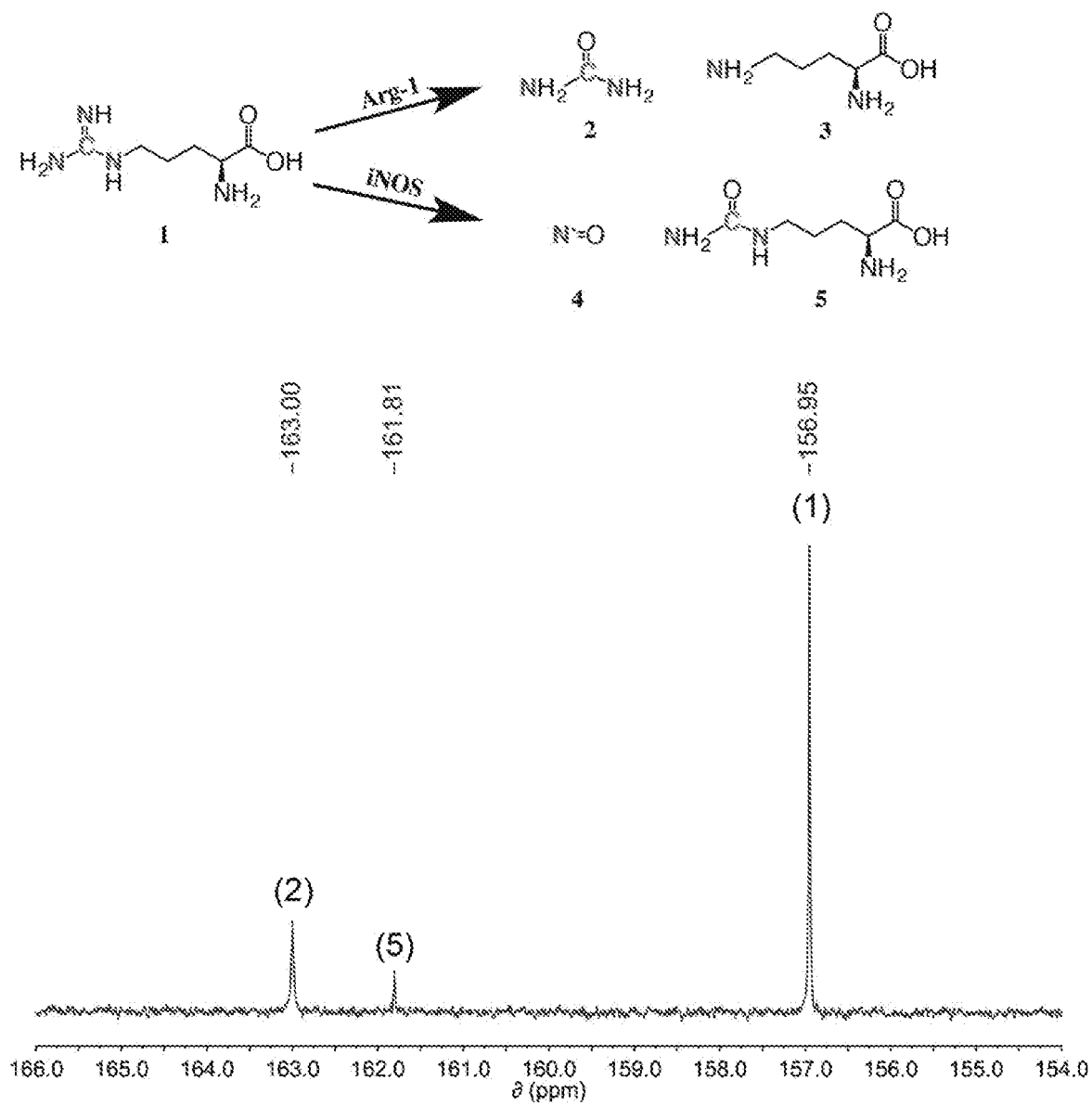
FIGS. 5A-5C show $^{13}C$ NMR spectra related to an illustrative embodiment of the present technology, [6-$^{13}C$, 6-$^{15}N_3$]-Arginine-HCl.

In some embodiments, the metabolite is produced by arginase and the hyperpolarized probe is a hyperpolarized compound of formula I, stereoisomer, tautomer, or pharmaceutically acceptable salt thereof, as described herein in any aspect or embodiment. FIG. 5A shows how in one embodiment the $^{13}C$ labeled guanidine carbon of a compound of formula I can be distinguished from its metabolites, urea (2) and cittruline (5) and monitored by $^{13}C$ NMR.

In some embodiments, the one or more mammalian cells include a tumor associated macrophage. In some embodiments, the tumor associated macrophage is a pro-inflammatory M1 macrophage. In certain embodiments, the M1 macrophages metabolize a hyperpolarized compound of formula I as described herein to produce a iNOS mediated metabolite. In one embodiment, the iNOS mediated metabolite includes nitric oxide. In another embodiment, the tumor associated macrophage is an anti-inflammatory M2 macrophage. In certain embodiments, the M2 macrophages metabolize a hyperpolarized compound of formula I as described herein to produce an arginase-1 mediated metabolite. In one embodiment, the arginase-1 mediated metabolites include urea, ornithine, citrulline or a mixture thereof.

In some embodiments, the metabolite is produced by xanthine oxidase and the hyperpolarized probe is a hyperpolarized compound of formula II or compound of formula III, a tautomer, or pharmaceutically acceptable salt, as described herein in any embodiment. In one embodiment, the xanthine oxidase metabolite includes uric acid.

In some embodiments, the one or more mammalian cells include one or more cancer cells. In some embodiments, the one or more cancer cells include, but are not limited to, one or more of renal, sarcoma, lung, prostate, breast, pancreatic, oral, or epithelial cancer cells.

In some embodiments, the composition is administered to a mammal. As used herein, the term mammal includes, but is not limited to, a cat, dog, rodent, or primate. In one embodiment, the mammal is a human. Typically, the composition is administered to a human suffering from or suspected of suffering from cancer. As used herein, a "subject" or a "patient" is a mammal as described herein. The term "subject" and "patient" can be used interchangeably "Effective amount" refers to the amount of a compound or composition required to produce a desired effect. One example of an effective amount includes amounts or dosages that yield acceptable toxicity and bioavailability levels for imaging and/or therapeutic (pharmaceutical) use including, but not limited to the treatment of cancer.

In another related aspect, the present technology provides methods of identifying a target of interest including contacting the target of interest with a detectable or imaging effective quantity of a compound of the present technology. In some embodiments, a method of imaging is provided that includes contacting one or more mammalian cells with an effective amount of a composition comprising a deuterium exchanged-hyperpolarized probe to one or more mammalian cells; and detecting (and optionally quantifying) by magnetic resonance the hyperpolarized probe and/or a metabolite of the probe in the one or more mammalian cells; where the deuterium exchanged-hyperpolarized probe is a deuterated compound of formula I, and/or stereoisomers thereof, and/or tautomers thereof, and/or pharmaceutically acceptable salts thereof, a deuterated compound of formula IV (IV)

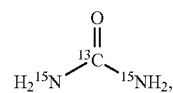

and/or tautomers thereof, or
a deuterated compound of formula V

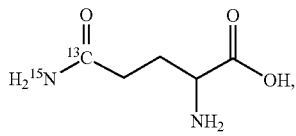
(V)

and/or stereoisomers thereof, and/or tautomers thereof, and/or pharmaceutically acceptable salts thereof; and the deuterated compound has been subjected to hyper polarization. In some embodiments, the deuterated compound exhibits a longer $T_1$ and $T_2$ relaxation time for a $^{13}C$-labeled carbon of a compound of formula I, a stereoisomer thereof, formula V, a stereoisomer thereof, or formula IV, and/or tautomers, and/or pharmaceutically acceptable salts thereof.

In some embodiments, the deuterated compound of formula I, and/or stereoisomers thereof, and/or tautomers thereof, and/or pharmaceutically acceptable salts thereof, is represented by a compound of formula VI

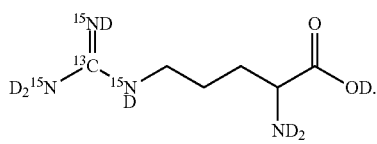
(VI)

In some embodiments, the deuterated compound of formula IV, and/or tautomers thereof, is represented by a compound of formula VIII,

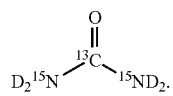
(VIII)

In some embodiments, the deuterated compound of formula V, and/or stereoisomers thereof, and/or tautomers thereof, and/or pharmaceutically acceptable salts thereof, is represented by a compound of formula VII

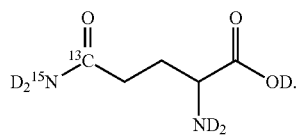
(VII)

In some embodiments, the metabolite is produced by arginase and the deuterium exchanged-hyperpolarized probe is a hyperpolarized compound of formula I, stereoisomer, tautomer, or pharmaceutically acceptable salt thereof, as described herein in any aspect or embodiment. FIG. 5A shows how in one embodiment the $^{13}C$ labeled guanidine carbon of a compound of formula I can be distinguished from its metabolites, urea (2) and cittruline (5) and monitored by $^{13}C$ NMR.

In some embodiments, the deuterium exchanged-hyperpolarized probe is deuterated hyperpolarized compound of formula IV, and/or the tautomer thereof, and/or the pharmaceutically acceptable salt of any of the preceding compounds, as described herein in any embodiment. In some embodiments, the deuterated hyperpolarized compound of formula IV, and/or the tautomer thereof, and/or the pharmaceutically acceptable salt may be absorbed by urea transporter enzymes. For example, urea transporter enzymes include, but are not limited to, UT-A and UT-B family of enzymes.

In some embodiments, the metabolite is produced by glutaminase, glutamine fructose-6-phosphate, glutamine-asparaginase, amidophosphoribosyltransferase aspartate carbamoyltransferase, glutamate synthase, or mixtures of two or more thereof, and the deuterium exchanged-hyperpolarized probe is deuterated hyperpolarized compound of formula V, and/or the stereoisomer thereof, and/or the tautomer thereof, and/or the pharmaceutically acceptable salt of any of the preceding compounds, as described herein in any embodiment. In some embodiments, the metabolite is produced by glutaminase, and the deuterium exchanged-hyperpolarized probe is deuterated hyperpolarized compound of formula V, and/or the stereoisomer thereof, and/or the tautomer thereof, and/or the pharmaceutically acceptable salt of any of the preceding compounds, as described herein in any embodiment.

In some embodiments, the one or more mammalian cells include a tumor associated macrophage as described herein in any embodiment. In some embodiments, the one or more mammalian cells include cancer cells as described herein in any embodiment. In some embodiments, the composition is administered to a mammal as described herein in any embodiment. In certain embodiments, the mammal is a human.

"Exchangeable proton" refers to protons covalently bonded to an atom that exchange with deuterium atoms upon exposure to an appropriate solvent, for example, deuterium oxide. The term "deuterium exchanged-hyperpolarized probe" or "deuterated compound" refers to a compound as described herein in any embodiment where the exchangeable protons have been exchanged with deuterium atoms. Exchangeable protons may be attached to nitrogen, oxygen or sulfur, e.g., amide or amine nitrogens, hydroxy oxygens, and thiol sulfurs. Exchangeable protons may also be attached in place of labile protons, e.g., protons attached to the alpha-carbon of an acyl group such as aldehyde, ketone or ester.

In another related aspect of the present technology, there are provided deuterium exchanged-hyperpolarized probes that include a compound of formula VI

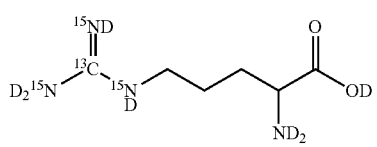
(VI)

or
a compound of formula VII

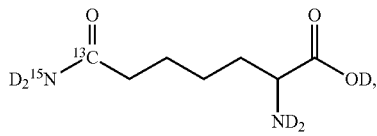

stereoisomers, tautomers, and/or pharmaceutically acceptable salts thereof. In some embodiments, the deuterium exchanged-hyperpolarized probe is a compound of formula VI, and/or stereoisomers thereof, and/or tautomers thereof, and/or pharmaceutically acceptable salts thereof. In some embodiments, the deuterium exchanged-hyperpolarized probe is a compound of formula VII, and/or stereoisomers thereof, and/or tautomers thereof, and/or pharmaceutically acceptable salts thereof.

The examples herein are provided to illustrate advantages of the present technology and to further assist a person of ordinary skill in the art with preparing or using the compounds of the present technology or salts, pharmaceutical compositions, derivatives, solvates, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

General Synthetic and Analytical Details

All reagents and materials are or were purchased from commercial vendors.

Example 1: Synthesis of $^{15}N,^{13}C$-Xanthine

Preparation of [2-$^{13}C$, 1,3-$^{15}N_2$]-3,7-dihydro-1H-purine-2,6-dione (6)

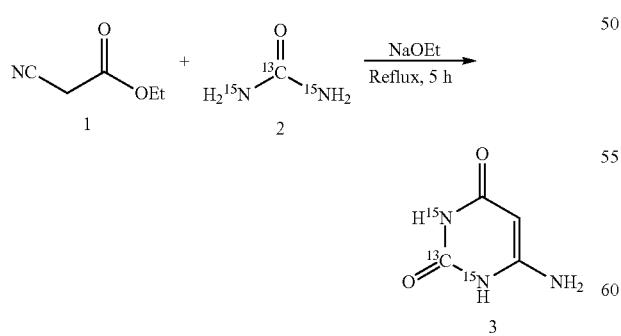

In an oven-dried round bottom flask equipped with a magnetic stir bar, 1.8 grams of sodium ethoxide was dissolved with 30 mL of ethanol. After complete dissolution, ethyl cyanoacetate (1, 1.9 g, 16.8 mmol) and ($^{15}N_2$, $^{13}C$)-urea (2, 1.05 g, 16.6 mmol) were added to the mixture. The reaction mixture was heated and stirred at reflux for 5 hours (81.5° C.). At the end of the reaction time, 20 mL of hot (80° C.) water is added. The stirred mixture is heated at 80° C. for an additional 15 minutes to give 6-aminopyrimidine-2-4(1H,3H)-dione (3).

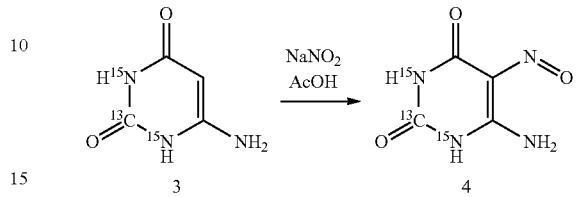

After cooling, the product (3) mixture was neutralized with 2 mL of acetic acid and an extra 1.6 mL of acetic acid was added to the mixture. Sodium nitrate (1.3 g, 18.8 mmol) was dissolved in 2 mL of water and added to the reaction mixture and stirred overnight at room temperature. At the end of the reaction time, the obtained purple solid (4) was filtered and wash with 2 mL of cold water.

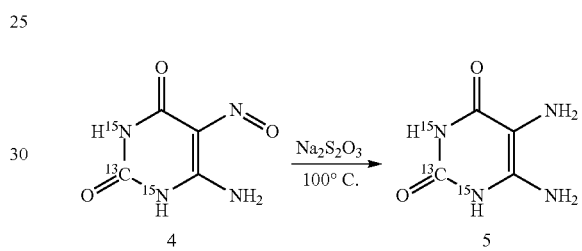

The purple solid (4) was suspended in water (15 mL) and heated to 90° C. 6 g of solid sodium dithionite was added to the suspension in portions. The bleached suspension is stirred for 15 minutes at 90° C. At the end of the reaction time the mixture is allowed to cool. The dense diaminouracil bisulfite is filtered from the cooled solution, washed well with water and dried under vacuum at 45° C. to give 5,6-diamino-2,4-dihydroxypyrimidine (5) as a pale brown powder.

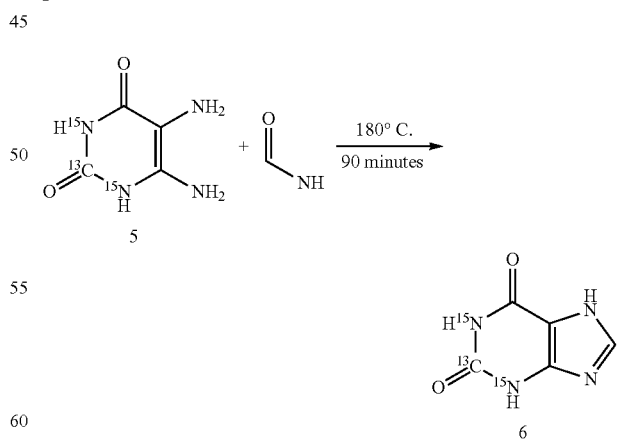

A suspension of 400 mg of 5,6-diamino-2,4-dihydroxypyrimidine (5) in 1.5 mL of formamide in high pressure flask was heated for 90 minutes at 180° C. The mixture was cooled, and the precipitate was filtered off and washed with water and cold ethanol and a yellow pale powder of xanthine (6) is obtained. Compound 6 is expected to exhibit mass spectrum and NMR data consistent with its structure.

Synthetic Scheme for Preparation of [5-$^{13}$C,7-$^{15}$N]-3,7-dihydro-1H-purine-2,6-dione (13)

Compound 13 was prepared following a similar procedure as described above for compound 6. The general schematic for preparation of compound 13 is illustrated below:

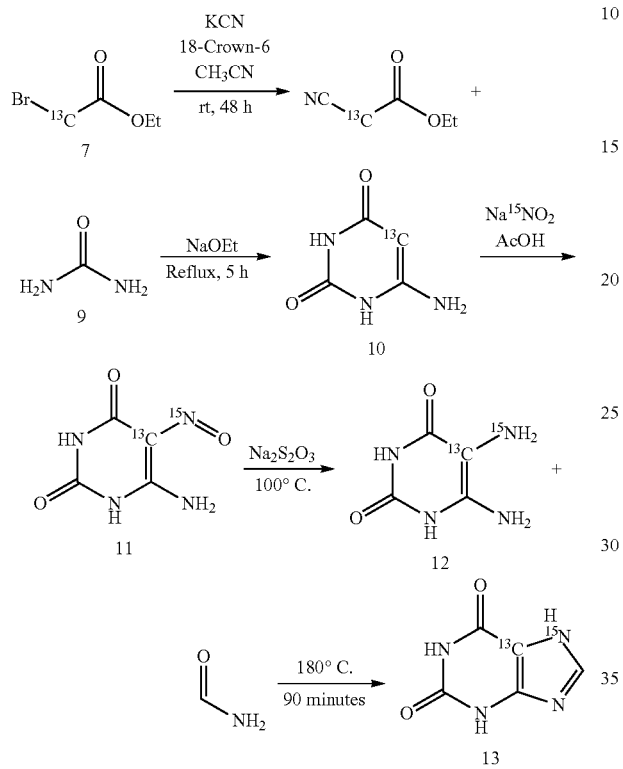

Example 2: Synthesis of [6-$^{13}$C, 6-$^{15}$N$_3$]-L-Arginine-HCl (21)

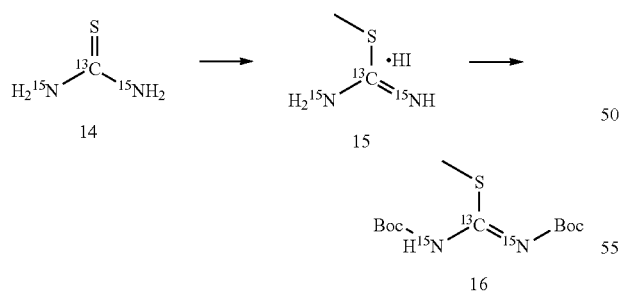

2-methylisothiouronium-$^{13}$C-$^{15}$N$_2$ iodide (15): In an oven-dried round bottom flask equipped with a magnetic stir bar, 2.5 g $^{13}$C, $^{15}$N$_2$-thiourea (14, 31.6 mmol, 1 equivalent) was dissolved in 100 mL MeOH. To this, 5.15 g iodomethane (36.3 mmol, 1.15 equivalents) was added and this reaction mixture was stirred at reflux for 3 hours. The reaction mixture was cooled to room temperature and concentrated under vacuum to give pure compound 15 as a white solid in 97% yield (6.7 g). $^1$H NMR (600 MHz, D$_2$O): δ=2.58 (d, 3H, $^3J_{H,C}$=4.9 Hz) ppm. $^{13}$C NMR (151 MHz, D$_2$O, MeOH reference): δ=173.3 (t, $^1J_{C,N}$=19.1 Hz), 13.6 ppm. HRMS (ESI) m/z calculated for C$^{13}$CH$_7$$^{15}$N$_2$S (M+H)$^+$ 94.0304, found 94.0304.

Methyl N,N'-bis(tert-butoxycarbonyl)carbamimidothioate-$^{13}$C-$^{15}$N$_2$ (16): An oven dried round bottom flask was equipped with a magnetic stir bar and charged with 4.7 g compound 15 (21.3 mmol, 1 equiv), 75 mL dichloromethane (DCM), and 71.5 mL saturated NaHCO$_3$ in H$_2$O. To this, 18.6 g di-tert-butyl dicarbonate (85.2 mmol, 4 equiv) was added and the reaction mixture was stirred at ambient temperature over 5 days. The reaction mixture was diluted with 120 mL 1:1 DCM:H$_2$O, the organic phase was collected, and the aqueous phase was extracted with DCM (2×100 mL). Pooled organic phase was washed with H$_2$O (2×120 mL) and brine (120 mL), dried with MgSO$_4$, and concentrated under vacuum. Crude product was purified by flash chromatography (3% diethylether in hexanes, V/V) and dried to yield a white solid (16) in 78.5% yield (4.9 g). $^1$H NMR (600 MHz, CDCl$_3$): δ=11.71 (d, 1H, $^1J_{H,N}$=90.6 Hz), 2.39 (d, 3H, $^3J_{H,C}$=4.8 Hz), 1.52 (s, 9H), 1.50 (s, 9H) ppm. $^{13}$C NMR (151 MHz, CDCl$_3$): δ=171.9-171.2 (m), 161.1-160.6 (m), 151.1-150.6 (m), 83.3, 81.1, 28.1, 14.5 (d, $^2J_{C,C}$=4.8 Hz) ppm. HRMS (ESI) m/z calculated for C$_{11}$$^{13}$CH$_{22}$Na$^{15}$N$_2$O$_4$S (M+Na)$^+$ 316.1172, found 316.1195.

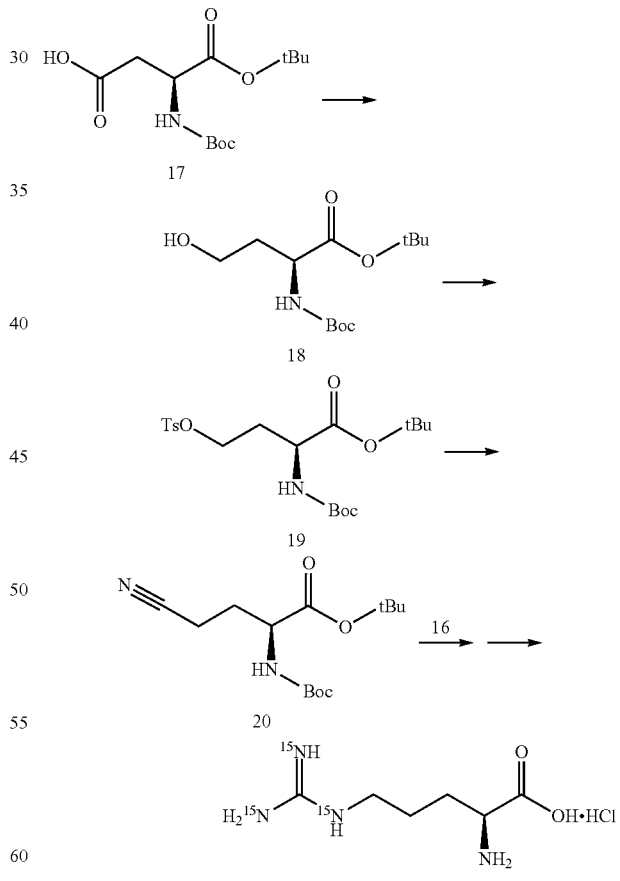

(tert-butyl (tert-butoxycarbonyl)-L-homoserinate (18): An oven dried 2-neck round bottom flask was equipped with a magnetic stir bar and an argon inlet. The flask was charged with 5 g compound 17(17.3 mmol, 1 equiv) and sealed under an argon atmosphere. 80 mL dry THF and 1.92 g triethylamine (19.0 mmol, 1.1 equiv) were added to the flask, and the mixture was cooled in an ice-salt bath between −5 and −10° C. To this, 2.06 g ethyl chloroformate (19.0 mmol, 1.1 equiv) was added dropwise as the reaction mixture was stirred vigorously. While continuing stirring, the mixture was subsequently removed from the ice bath and allowed to equilibrate to ambient temperature over 30 minutes, after which the reaction mixture was filtered and set aside. Meanwhile a second round bottom flask was equipped with a stir bar and charged with 1.37 g sodium borohydride (36.3 mmol, 2.1 equiv) and 10 mL $H_2O$. This was cooled in an ice bath and the filtrate from the first reaction was added dropwise while stirring vigorously. After all the filtrate was added, the flask was removed from the ice bath and stirred at ambient temperature for 1 hour. The reaction mixture was washed with saturated $NaHCO_3$ (1×100 mL). The organic phase was collected, and the aqueous phase was extracted with EtOAc (3×100 mL). Crude product was purified by flash chromatography (20:80 EtOAc:Hexanes, V/V) and dried, affording a yellow oil (18) in 83% yield (4.2 g). $^1H$ NMR (600 MHz, $CDCl_3$): δ=5.35 (d, 1H, $^3J_{H,H}$=7.2 Hz), 4.39-4.29 (1H, m), 3.73-3.58 (2H, m), 2.17-2.08 (m, 1H), 1.57-1.47 (m, 1H), 1.45 (s, 9H), 1.43 (s, 9H) ppm. $^{13}C$ NMR (151 MHz, $CDCl_3$): δ=172.1, 156.8, 82.4, 80.5, 77.4, 77.2, 77.0, 58.3, 51.0, 36.7, 28.4, 28.1 ppm. HRMS (ESI) m/z calculated for $C_{13}H_{25}NaNO_5$ $(M+Na)^+$ 298.1629, found 298.1630.

tert-butyl N-(tert-butoxycarbonyl)-O-tosyl-L-homoserinate (19): To an oven dried round bottom flask equipped with a magnetic stir bar, 3.7 g compound 18 (13.4 mmol, 1 equiv) and 6.78 g triethylamine (67 mmol, 5 equiv) were dissolved in 25 mL DCM and cooled in an ice bath. After cooling, 5.11 g p-toluenesulfonyl chloride (26.8 mmol, 2 equiv) and 0.164 g DMAP (1.34 mmol, 0.1 equiv) were added and the reaction mixture was stirred at room temperature for 1 hour. The reaction mixture was subsequently diluted with 100 mL DCM and washed with $H_2O$ (4×60 mL), brine (1×60 mL), dried with $MgSO_4$, and concentrated under vacuum. Crude product was purified via flash chromatography (3:7 EtOAC: Hexanes, V/V) and dried under vacuum to yield a white tacky solid (19) in 76% yield (4.4 g). $^1H$ NMR (600 MHz, $CDCl_3$): δ=7.74 (d, 2H, $^3J_{H,H}$=7.8 Hz), 7.31 (d, 2H, $^3J_{H,H}$=7.8 Hz), 5.04 (d, 1H, $^3J_{H,H}$=7.8 Hz), 4.19-4.08 (m, 1H), 4.08-3.95 (m, 2H), 2.40 (s, 3H), 2.23-2.06 (m, 1H), 2.06-1.93 (m, 1H), 1.40 (s, 9H), 1.36 (s, 9H) ppm. $^{13}C$ NMR (151 MHz, $CDCl_3$): δ=170.6, 155.2, 144.9, 132.7, 129.9, 128.0, 82.6, 79.8, 77.4, 77.2, 77.0, 66.6, 51.0, 31.5, 28.3, 27.9, 21.6 ppm. HRMS (ESI) m/z calculated for $C_{20}H_3$, $NaNO_7S$ $(M+Na)^+$ 452.1722, found 452.1719.

tert-butyl (S)-2-((tert-butoxycarbonyl)amino)-4-$^{15}N$-(cyano)butanoate (20): An oven-dried round bottom flask was equipped with a magnetics stir bar and charged with 4.4 g compound 19 (10.2 mol, 1 equiv), 3.06 g NaI (20.4 mmol, 2 equiv), and 50 mL acetone. This mixture was stirred at reflux for 1 hour, cooled to room temperature, and diluted in 25 mL DCM. The reaction mixture was filtered, and the orange filtrate was dried under vacuum. The dry filtrate was diluted in an additional 90 mL DCM, filtered, and the filtrate was dried under vacuum in a round bottom flask. The flask containing the dry filtrate was equipped with a magnetic stir bar and charged with 50 mL DMSO and 0.809 g $KC^{15}N$ (12.2 mmol, 1.2 equiv). The flask was placed in an oil bath set to 80° C. and the reaction mixture was stirred under a reflux condenser for 18 hours. Afterwards, the magnetic stir bar was removed, the reaction mixture was frozen, and the DMSO was removed under reduced pressure with a lyophilizer. The dried reaction mixture was diluted in 200 mL $H_2O$ and extracted with EtOAc (3×200 mL) and the pooled organic phase was washed with $H_2O$ (2×300 mL) and brine (1×300 mL). The organic phase was dried under vacuum, and the crude product was purified with flash chromatography (2:8 EtOAc:Hexanes, V/V), yielding a white solid in 52% yield (1.5 g). $^1H$ NMR (600 MHz, $CDCl_3$): δ=5.17 (d, 1H, $^3J_{H,H}$=6 Hz), 4.27-4.15 (m, 1H), 2.51-2.33 (m, 2H), 2.31-2.18 (m, 1H), 2.01-1.89 (m, 1H), 1.48 (s, 9H), 1.44 (s, 9H) ppm. $^{13}C$ NMR (151 MHz, $CDCl_3$): δ=170.3, 155.5, 119.1 (d, =16.9 Hz), 83.3, 80.4, 77.4, 77.2, 77.0, 54.0, 53.1, 29.3, 28.4, 28.1, 13.8, 13.8 ppm. HRMS (ESI) m/z calculated for $C_{14}H_{24}NaN^{15}NO_4$ $(M+Na)^+$ 308.1604, found 308.1597.

tert-butyl (E)-$N^2,N^\omega,N^{\omega'}$-tris(tert-butoxycarbonyl)-L-argininate-$C^\omega$-$^{13}C$—$N^\delta$, $N^\omega,N^{\omega'}$-$^{15}N$: To an oven dried round bottom flask equipped with a magnetic stir bar, 1.7 g compound 20 (5.96 mmol, 1 equiv) and 45 mL acetic acid was added. 1.26 g 10% Pd/C (dry basis, ~50% water, approx. 0.1 equiv Pd) was added and the flask and the reaction mixture was sealed in a Parr apparatus. While stirring, a vacuum was pulled in the Parr apparatus for 5 minutes. The Parr apparatus was subsequently charged with 70 PSI $H_2$ and the reaction mixture was stirred at room temperature for 2 hours. After this time, $H_2$ gas was released from the vessel outlet and residual $H_2$ gas was removed by exposing the reaction mixture to a vacuum while stirring for 5 minutes. The Parr apparatus was subsequently opened, the magnetic stir bar was removed, the reaction mixture was frozen, and acetic acid was removed under reduced pressure in a lyophilizer. The remaining oil was the acetate salt of the reduced nitrile (confirmed by NMR) and was used for the next step without purification. The oil was added to an oven dried round bottom flask equipped with a magnetic stir bar, which was combined with 50 mL DMSO, 1.92 g compound 16 (6.56 mmol, 1.1 equiv), and 3.02 g triethylamine (29.8 mmol, 5 equiv). This reaction mixture was stirred at ambient temperature for 24 hours after which the stir bar was removed, the mixture was frozen and dried under reduced pressure in a lyophilizer. The crude product was purified via flash chromatography (2:8 EtOAc:Hexanes, V/V) to yield a light yellow oil in 54% yield (1.73 g). $^1H$ NMR (600 MHz, $CDCl_3$): δ=11.47 (d, 1H, $^1J_{H,N}$=91.8 Hz), 8.45-8.23 (m, 1H), 5.16-4.99 (m, 1H), 4.23-4.09 (m, 1H), 3.45-3.33 (m, 2H), 1.88-1.73 (m, 1H), 1.68-1.59 (m, 2H), 1.59-1.50 (m, 1H), 1.47 (s, 9H), 1.46 (s, 9H), 1.44 (s, 9H), 1.42 (s, 9H) ppm. $^{13}C$ NMR (151 MHz, $CDCl_3$): δ=171.7, 163.6-162.9 (m), 156.2 (d,d,d, $^1J_{C,N}$=8.38 Hz, $^1J_{C,N}$=14.4 Hz, $^1J_{C,N}$=24.6 Hz), 83.3, 82.1, 79.8, 79.5, 53.6, 40.7-40.1 (m), 30.3 ppm, 28.4, 28.4, 28.1, 28.1, 24.9 ppm. HRMS (ESI) m/z calculated for $C_{24}^{13}CH_4N^{15}N_3O_8$ $(M+H)^+$ 535.3314, found 535.3338.

[6-$^{13}C$, 6-$^{15}N_3$]-L-Arginine-HCl (21): An oven dried round bottom flask was equipped with a magnetic stir bar and charged with 1.73 g of tert-butyl (E)-$N^2,N^\omega,N^{\omega'}$-tris (tert-butoxycarbonyl)-L-argininate-$C^\omega$-$^{13}C$—$N^\delta,N^\omega,N^{\omega'}$-$^{15}N$ (3.23 mmol). To this, 100 mL 1:9 trifluoroacetic acid: DCM was added and the solution was stirred at ambient temperature for 18 hours. The mixture was dried under reduced pressure, 120 mL 1:1 DCM:H2O was added to the flask and the solution was transferred to a separatory funnel. The aqueous layer was collected, and the organic phase was extracted with $H_2O$ (2×50 mL). Aqueous fractions were pooled, washed with 70 mL DCM, and dried under reduced pressure. The trifluoroacetate counter-ion was exchanged with a chloride counter-ion through 3 cycles of treatment with 100 mL 1M HCl and subsequent drying under reduced pressure. 640 mg of crude product remained, which was redissolved in 349 mg aniline (3.25 mmol) and 3 mL 90% EtOH in H$_2$O at 50° C. This solution was left undisturbed at room temperature for 24 hours as [6-$^{13}$C, 6-$^{15}$N$_3$]-Arginine-HCl crystallized out of solution. The resulting white solid was collected and washed with cold 90% EtOH in H$_2$O and dried in an oven for 3 hours, yielding the pure monochloride salt as a white powder in 53.2% yield (568 mg). $^1$H NMR (600 MHz, D$_2$O): δ=3.74 (t, 1H, $^2J_{C,N}$=1 Hz), 3.25-3.15 (m, 2H), 1.93-1.82 (m, 2H), 1.74-1.55 (m, 2H) ppm. $^{13}$C NMR (151 MHz, D$_2$O, MeOH Reference): δ=174.9 ppm, 157.3 (q, $^1J_{C,N}$=22.1 Hz), 54.9, 41.1 (d, 9.1 Hz), 28.2, 24.5 ppm. HRMS (ESI) m/z calculated for C$_{12}$$^{13}$CH$_{15}$N$^{15}$N$_3$O$_2$ (M+H)$^+$ 179.1139, found 179.1140. Melting point measured at 218° C.

Example 3: Xanthine Oxidase (XO) Activity Evaluation Using Hyperpolarized $^{13}$C, $^{15}$N-Xanthine Probes Hyperpolarized Imaging A preparation containing 0.15-0.2 M [2-$^{13}$C, 1,3-$^{15}$N$_2$]-3,7-dihydro-1H-purine-2,6-dione (6, as described in Example 1) and the OX063 radical was hyperpolarized using a SPINlab hyperpolarizer. T1 measurements were performed using 1T Magritek Spectrometer. For the acquisition of hyperpolarized spectra, data was acquired with a 5 s repetition time and 15° excitation for a total of 45 s. In vitro enzymatic experiments to evaluate the activity of XO in oxidizing xanthine (XA) to uric acid (UA) using superoxide as a cofactor were performed using 100 mg of mouse liver extract together with a PMS/NADH+ system to generate O$^{2-}$. $^{13}$C NMR spectra was acquired using a 14.1T NMR spectrometer.

Figure 2:
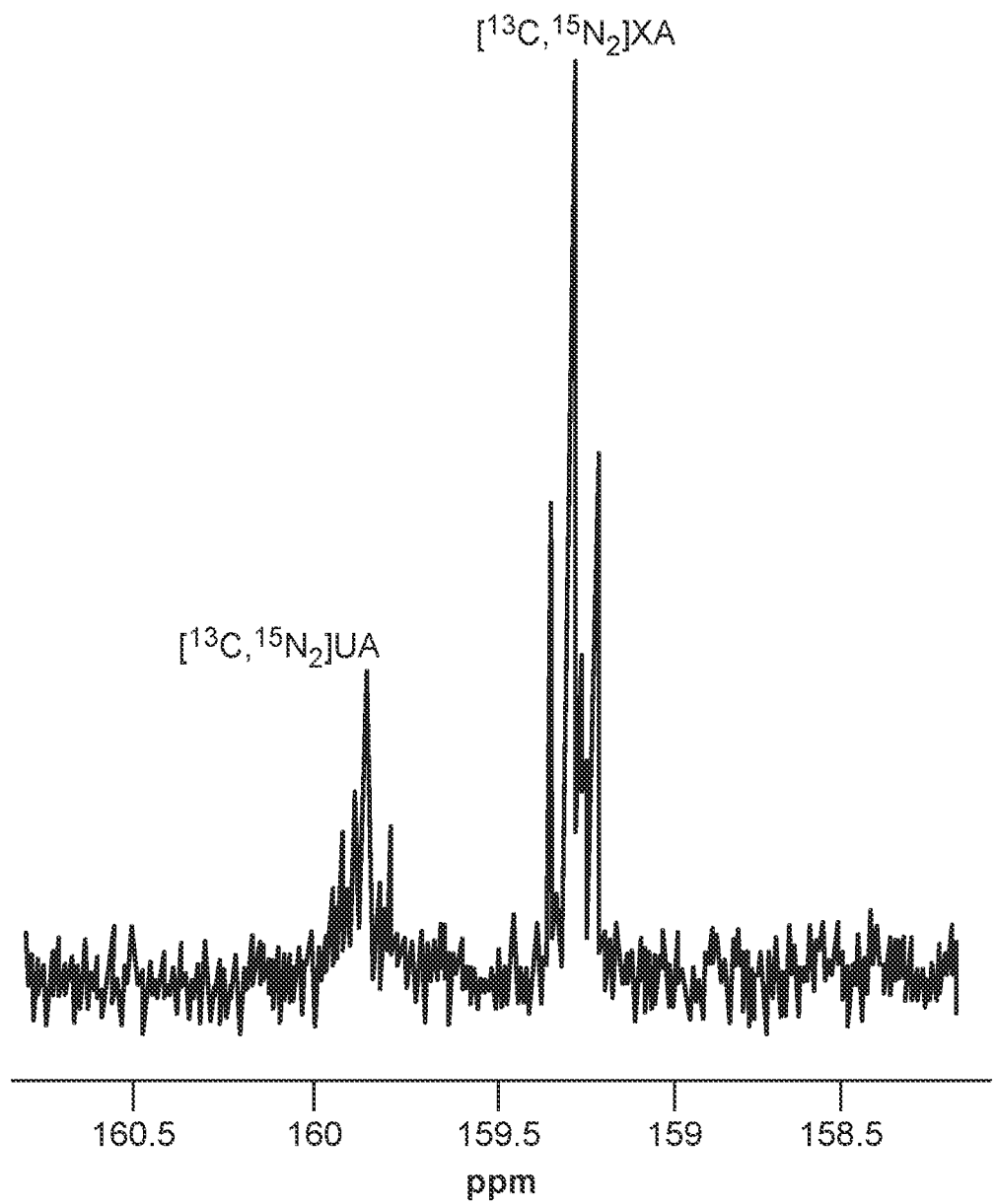
FIG. 2 shows the in vitro $^{13}C$ NMR spectra of hyperpolarized compound 6 and uric acid metabolite in the presence of liver extracts and $O^{2-}$.

Compound 6 was hyperpolarized. The $^{13}$C chemical shift between hyperpolarized XA and hyperpolarized UA was measured and determined to be 0.8 ppm. After dissolution, spectra of compound 6 were obtained and fit to a monoexponential decay function, correcting for flip angle, to determine the spin-lattice relaxation time. A T1 of 77±1.4 s was measured (FIG. 2). Additional in vitro NMR experiments demonstrated that compound 6 could be oxidized in less than 10 minutes to urea in liver extracts in the presence of O$^{2-}$. These results show that compound 6 has a long T1 and differential chemical shift, and is expected to be useful for imaging in vivo.

Antioxidant Activity

Figure 3:
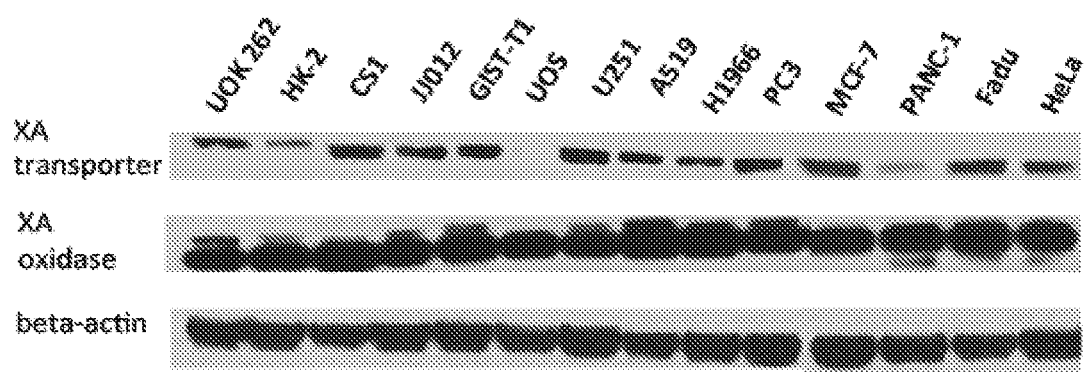
FIG. 3 shows expression levels of xanthine transporter and xanthine oxidase across 14 cell lines.
Figure 4:
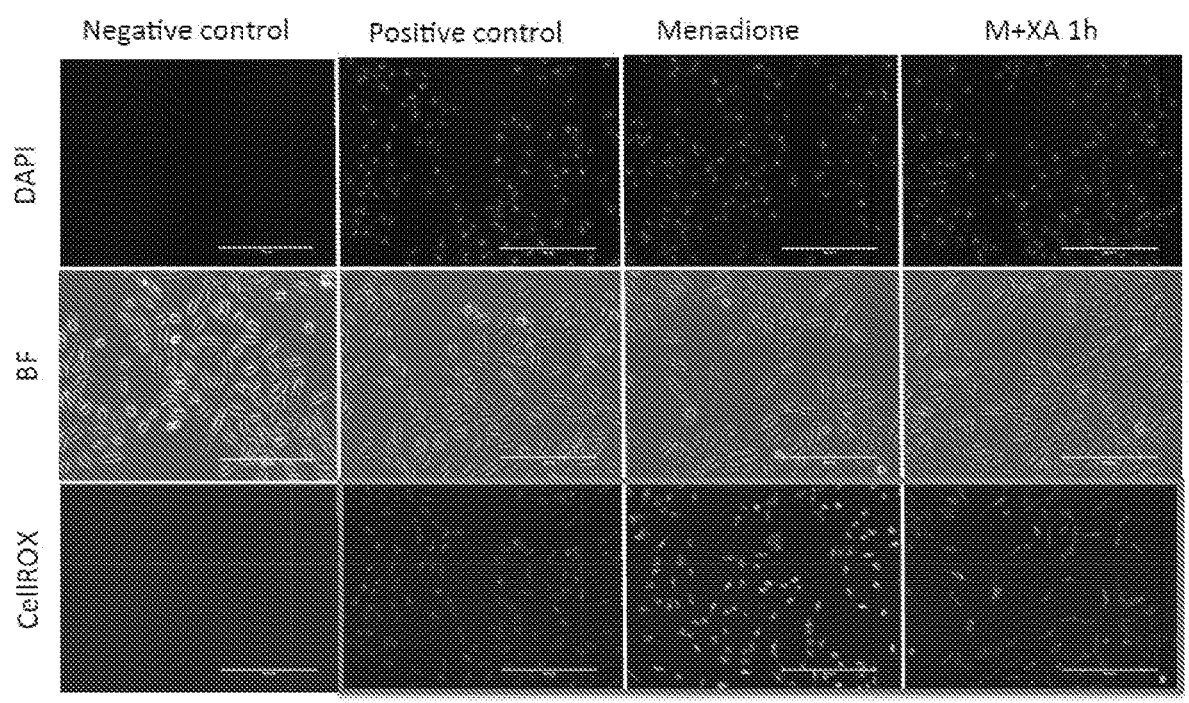
FIG. 4 shows a panel of fluorescent images, using Cell-Rox as an indicator of oxidative stress, treatment with menadione to increase oxidative stress, and reduction of oxidative stress after exposure to hyperpolarized Compound 6.

Western blots for XO and xanthine transporter were performed using 20 ng of protein extract from 14 cell lines. In vitro fluorescent microscopy using CellROX green was performed in U251 cells to evaluate intracellular reactive oxygen species (ROS) and the effect of xanthine as an ROS scavenger. 14 different cancer cell lines from renal, sarcoma, lung, prostate, breast, pancreatic, oral, epithelial cancer were also screened to evaluate expression of xanthine transporter and XO. In all the cells, a high expression of XO was observed, whereas xanthine transporter was variable between the cell lines, with the largest expression in U251 cells. Therefore, this cell line was used for further in vitro fluorescence experiments (FIG. 3). FIG. 4 shows a panel of fluorescent images, using CellRox as an indicator of oxidative stress, treatment with menadione dramatically increases oxidative stress and this can be reduced using co-incubation with compound 6 for 45 min, demonstrating that compound 6 can rapidly participate in this enzymatically catalyzed antioxidant system. Exemplary compounds of formula II or formula III of the present technology demonstrated the potential for hyperpolarized xanthine to probe an enzymatically catalyzed antioxidant system, which is specific to O$^{2-}$.

Example 4: Arginase Activity Evaluation Using Hyperpolarized [6-$^{13}$C,6$^{15}$N$_3$]-Arginine Hyperpolarized Imaging To confirm the reduction of quadrupolar relaxation at the guanidine-carbon by $^{15}$N enrichment, $^{13}$C NMR spectra for unlabeled and [6-$^{13}$C, 6-$^{15}$N$_3$]-L-Arginine-HCl (21, as described in Example 2) was obtained with a 14.1T $^{13}$C NMR. The full width half max (FWHM) of the guanidine-carbon peak was measured, and the FWHM of the carbon-1 peak was used as an internal standard. For hyperpolarized T$_1$ measurements compound 21 was mixed with 1 equivalent HCl and dissolved to a final concentration of 1.3 M in 2:3 H$_2$O:glycerol with 15 mM of a OX063 radical. The sample was polarized for at least 1 h in a SpinSolve polarizer. The T$_1$ for the arginine guanidine-carbon was calculated via acquisition of dynamic single-scan $^{13}$C NMR spectra with a 30° flip angle and 3 s repetition time starting approximately 30 s after dissolution using a Magnitek 1T NMR, and peak integral versus time was fit to an exponential decay formula correcting for hyperpolarization loss from the flip angle. This was performed twice and the calculated T$_1$ values were averaged.

Figure 5B:
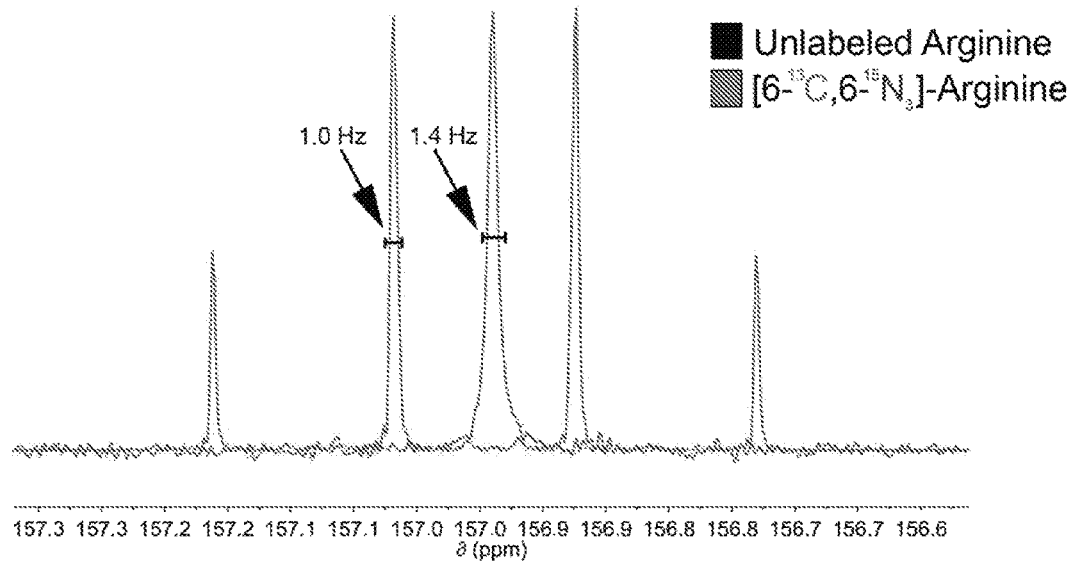
Figure 5C:
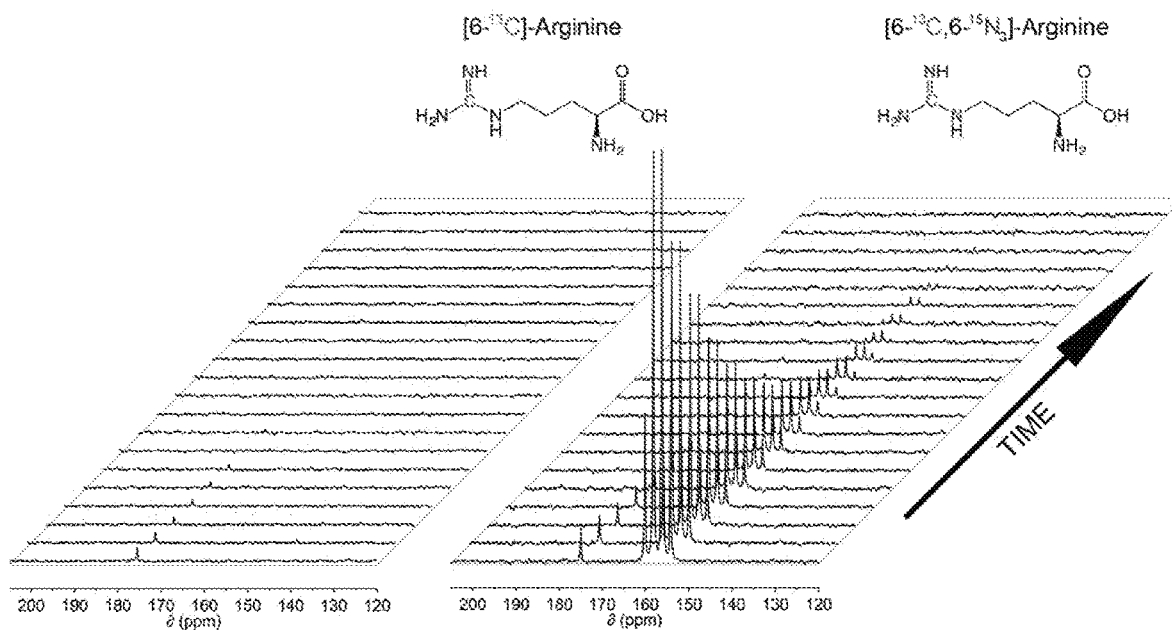

The FWHM of the guanidine-carbon peak for natural abundance and compound 21 was measured to be 1.4 Hz and 1.0 Hz, respectively, and the FWHM of carbon-1 was 0.9 Hz for both compounds (FIG. 5B). The T$_1$ of the guanidine-carbon of [6-$^{13}$C]-Arginine could not be measured due to quadrupolar relaxation, and the T$_1$ of the guanidine-carbon of compound 21 was calculated to be 20.4±0.4 s (FIG. 5C).

The FWHM$_{guanidine}$:FWHM$_{carbon-1}$ ratio decreased by 29% in the labeled compound, confirming that $^{15}$N labeling of arginine reduces quadrupolar relaxation at the guanidine-position. The dynamic HP $^{13}$C NMR data reveals the importance of $^{15}$N labeling of guanidine-nitrogens towards mitigating quadrupolar relaxation and extending hyperpolarized signal lifetime. By tracking the fate of arginine's carbon-6 via $^{13}$C MRS, it is possible to monitor its conversion to urea (via Arg-1) or citrulline (via iNOS), as demonstrated in the NMR spectrum in FIG. 5A. Therefore, the present methods may be used to follow Arg-1 activity within a tumor and serve as a surrogate readout of TAM infiltration. As such, this information may be used in therapy selection, monitoring therapeutic efficacy, and determining prognosis.

Arginase Activity Assay

Michaelis-Menten enzyme kinetics of human recombinant arginase-1 at 37° C. with natural abundance arginine or compound 21 as the substrate was measured using the colorimetric urea assay protocol of Knipp et al., *Anal. Biochem.* 286:257-64 (2000). Compound 21 (K$_m$=2.04±0.27 mM; V$_{max}$=48.2±2.0 s$^{-1}$) showed no significant difference in enzyme kinetics compared to natural abundance arginine (K$_m$=2.17±0.25 mM; V$_{max}$=54.8±2.2 s$^{-1}$). Therefore, heavy atom isotope effects were not observed for these metabolic reactions.

Figure 6:
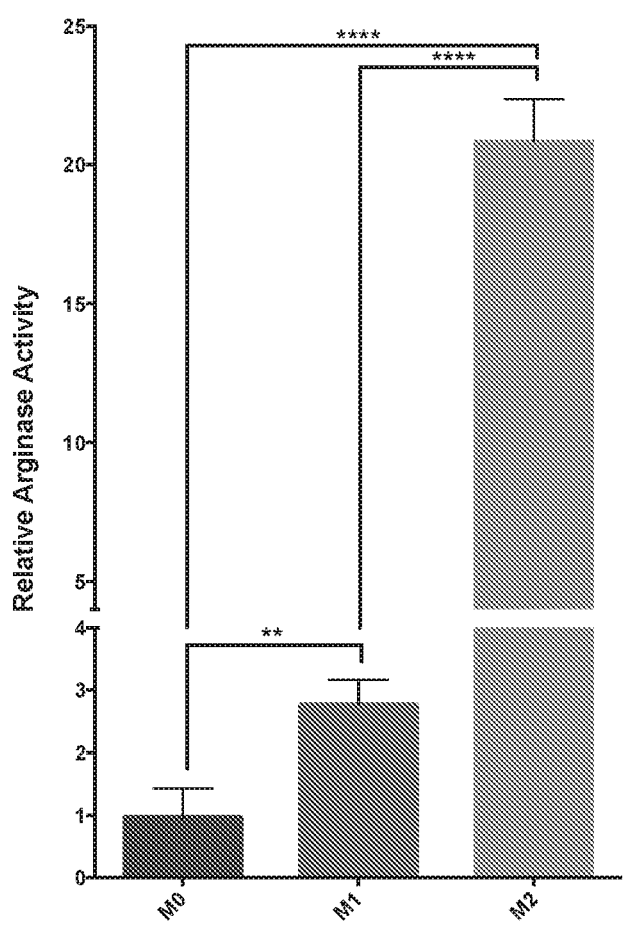
FIG. 6 shows the relative arginase activity of undifferentiated Raw 264.8 macrophages (MO), and M1 or M2 differentiated Raw 264.8 macrophages.

In vitro Arg-1 enzyme activity was measured using murine Raw 264.8 macrophages. These cells were differentiated into M1 and M2 lineages via a protocol detailed by Liu et al[9]. Arginase activity was measured using an Arginase activity kit (Sigma) on cell lysate, and activity values were normalized to total protein content measured by a bicinchoninic acid (BCA) assay (Thermo Fisher). Macrophages can be classified as pro-inflammatory (M1) or anti-inflammatory (M2) macrophages. These two cell types can be differentiated by the manner in which they metabolize arginine, where M1 macrophages favor iNOS mediated nitric oxide production while M2 macrophages overexpress Arginase-1 (Arg-1), which converts arginine to urea and ornithine. M2-differentiated murine macrophages exhibit approximately 7-fold increased arginase activity compared to M1-macrophages, and a 20-fold increase compared to undifferentiated Raw 264.8 macrophages (FIG. 6). The arginase activity assay data demonstrates the establishment of an in vitro model for low and high arginase-expressing cells.

Figure 10:
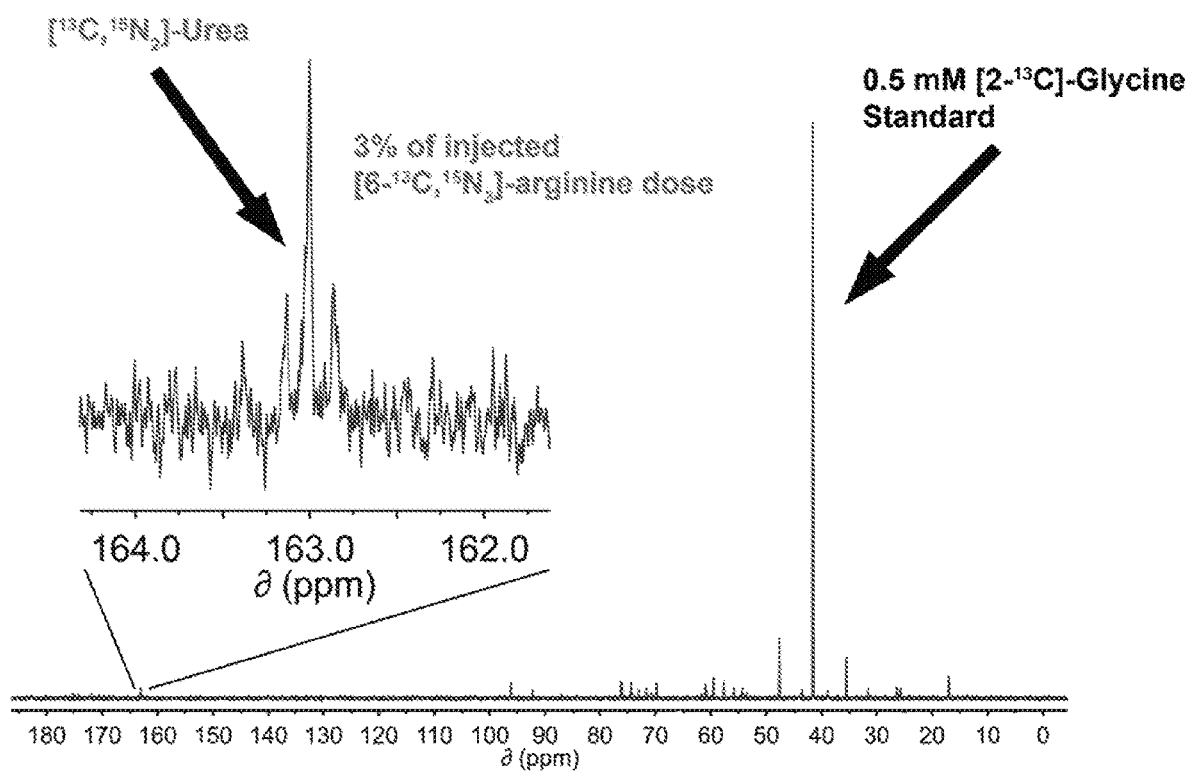
FIG. 10 shows a $^{13}$C-NMR spectrum of a mouse liver extract which contains a 0.5 mM glycine standard as a concentration reference.

In vivo assay: A female, Balb/c mouse was equipped with a tail vein cannula and placed under anesthesia (1.5% isoflurane, 1 L/min for 30 mins), after which it was injected with 250 µL 20 mM [6-$^{13}$C, $^{15}$N$_3$]-arginine in 100 mM Tris, 1 mM EDTA pH 7.4 (in addition to another 100 µL of 10 U/mL heparin in saline which was in the dead space of the cannula) over the course of 10 seconds. 1 minute post-injection, the mouse was sacrificed via cervical dislocation, and the liver was collected and frozen in liquid nitrogen. 118 mg of the liver was extracted in 4% perchloric acid, the metabolite extract mixture was dried and subsequently re-suspended in D$_2$O containing the glycine standard and 0.5 mM Gd-DOTA. A $^{13}$C-NMR spectrum was acquired on a 600 MHz spectrometer (FIG. 10). As shown in FIG. 10, the moles of [$^{13}$C, $^{15}$N$_2$]-urea in the sample was calculated by comparing the peak integral to that of the glycine standard. When extrapolating this value to a 1 g liver, the amount of [$^{13}$C, $^{15}$N$_2$]-urea produced after 1 min corresponds to approx. 3% of the total injected arginine dose.

Example 5: Dissolution of Hyperpolarized Probes in D$_2$O $T_1$ and $T_2$ Measurement at High Field (14.1T)

[5-$^{13}$C]-glutamine (Cambridge Isotope Laboratories), [$^{13}$C]-urea (Sigma Aldrich), [$^{13}$C, $^{15}$N$_2$]-urea (Sigma Aldrich), [6-$^{13}$C]-arginine (Cambridge Isotope Laboratories), [5-$^{13}$C, $^{15}$N]-glutamine (24) (24, as described in Example 7) and [6-$^{13}$C, $^{15}$N$_3$]-arginine (21, as described in Example 2) were evaluated to determine thermal equilibrium $T_1$ and $T_2$. An aliquot of each compound was dissolved in 95:5 D$_2$O:H$_2$O containing 100 mM Tris pD 7.4 and 100% H$_2$O containing 100 mM Tris pH 7.4. [$^{13}$C]-urea and [$^{13}$C, $^{15}$N$_2$]-urea were dissolved to a final concentration of 100 mM. [5-$^{13}$C]-glutamine, [5-$^{13}$C, $^{15}$N]-glutamine (24), [6-$^{13}$C]-arginine, and [6-$^{13}$C, $^{15}$N$_3$]-arginine (21) while the glutamine and arginine variants were dissolved to a final concentration of 50 mM.

$^{13}$C NMR spectra for each compound dissolved in 95:5 D$_2$O:H$_2$O and 100% H$_2$O was obtained with a 14.1T $^{13}$C NMR (Bruker, USA). For inversion recovery experiments, 13 to 15 different delay times between the 180° and 90° pulses, spanning $3T_1$, were sampled. Each spectrum was an average of 3 to 4 scans, and a $5T_1$ to $6T_1$ pre-scan wait time was used to allow re-polarization of carbon nuclear spins between scans. $T_2$ values were measured using a Carr-Purcell-Meiboom-Gill (CPMG) sequence for each compound dissolved in 95:5 D$_2$O:H$_2$O and 100% H$_2$O. A 10 ms (or 5 ms $^{13}$C-urea samples) wait-time between 180° pulses was used, and signal was acquired at total echo times spanning $3T_2$. For both $T_1$- and $T_2$-relaxation curve fitting, spectra were imported into Mnova (Mestrelabs, USA) and the area under the curve (AUC) of the $^{13}$C resonance of interest was integrated. AUC values were exported to Prism 7 (GraphPad Software, USA), plotted against time on the x-axis, and data points were fit to the Bloch equations for $T_1$ and $T_2$.

Figure 7:
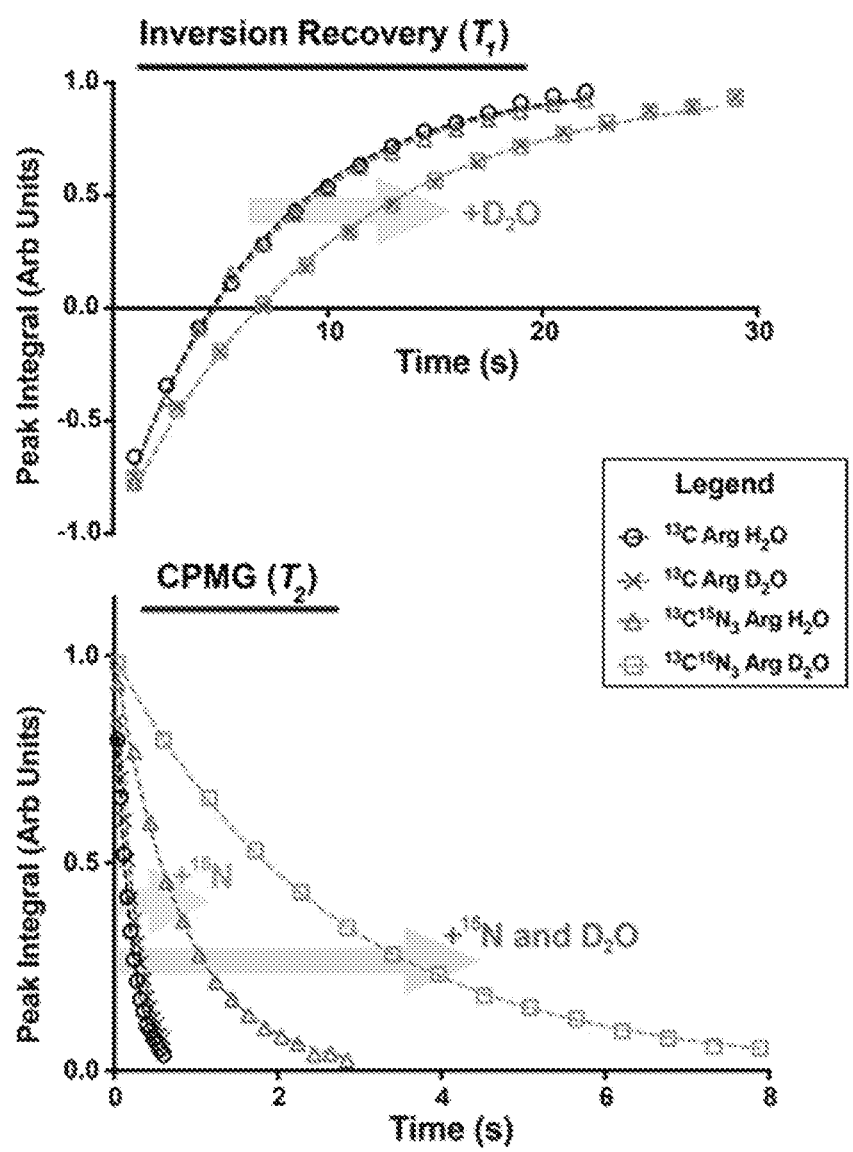
FIG. 7 shows the inversion recovery and Carr-Purcell-Meiboom-Gill (CPMG) acquisitions on arginine carbon-6 resonance for 6-$^{13}C$ or 6-$^{13}C$, $^{15}N_3$ labeled arginine dissolved in buffered $H_2O$ or $D_2O$ to measure $T_1$ and $T_2$ in a 14.1T field.

When each compound was dissolved in D$_2$O, the exchangeable protons on the nitrogen atoms rapidly exchange with deuterium in the solvent. As described in Table 1, at high field, each compound having protons exchanged with deuterium extended the $T_1$ of $^{13}$C relaxation times directly bonded to —NH or —NH$_2$ residues, respectively. This effect is further illustrated for [6-$^{13}$C]-/[6-$^{13}$C, $^{15}$N$_3$]-arginine in FIG. 7. No difference was exhibited for compounds when the adjacent nitrogen atom was $^{14}$N (99.6% natural abundance) or $^{15}$N. In contrast, as shown in Table 1, the presence of D$_2$O and $^{15}$N both play a role in extending carbon-$T_2$ for high field $T_2$. In the absence of $^{15}$N, the addition of D$_2$O leads to a slight increase in $T_2$. $^{15}$N enrichment dramatically increased carbon-$T_2$ even when H$_2$O is used as the solvent, and a more pronounced $T_2$ enhancement can be appreciated when this variant is dissolved in D$_2$O, as illustrated for arginine in FIG. 7. Thus, the present technology exhibits extended $T_1$ for deuterium exchanged hyperpolarized probes for the illustrative compounds, and compounds having both deuterium exchanged protons and $^{15}$N enrichment surprisingly showed an increased $T_2$.

TABLE 1

| Compound | Labeling | H$_2$O Value (s) | D$_2$O Value (s) | |
|---|---|---|---|---|
| Glutamine | $^{13}$C | 10.66 ± 0.34 | 12.34 ± 0.21 | $T_1$ |
| | $^{13}$C, $^{15}$N | 10.79 ± 0.34 | 12.29 ± 0.32 | |
| Urea | $^{13}$C | 31.01 ± 1.18 | 57.24 ± 3.95 | |
| | $^{13}$C, $^{15}$N$_2$ | 31.97 ± 1.38 | 57.34 ± 2.04 | |
| Arginine | $^{13}$C | 6.62 ± 0.22 | 9.74 ± 0.32 | |
| | $^{13}$C, $^{15}$N$_3$ | 6.83 ± 0.19 | 9.71 ± 0.26 | |
| Glutamine | $^{13}$C | 0.354 ± 0.003 | 0.455 ± 0.004 | $T_2$ |
| | $^{13}$C, $^{15}$N | 3.35 ± 0.21 | 4.66 ± 0.67 | |
| Urea | $^{13}$C | 0.089 ± 0.001 | 0.100 ± 0.002 | |
| | $^{13}$C, $^{15}$N$_2$ | 20.12 ± 0.17 | 34.61 ± 0.64 | |
| Arginine | $^{13}$C | 0.184 ± 0.003 | 0.234 ± 0.004 | |
| | $^{13}$C, $^{15}$N$_3$ | 0.82 ± 0.02 | 2.68 ± 0.03 | |

Hyperpolarized Imaging

Each compound was prepared with a different formulation, as follows: [5-$^{13}$C]- and [5-$^{13}$C, $^{15}$N]-glutamine was mixed with 1.1 equivalent HCl and dissolved to a final concentration of 1.5 M in H$_2$O:DMSO (65:35). [$^{13}$C]— and [$^{13}$C, $^{15}$N$_2$]-urea was dissolved to a final concentration of 6M in glycerol. [6-$^{13}$C]- and [6-$^{13}$C, $^{15}$N$_3$]-arginine was mixed with 1 equivalent HCl and dissolved to a final concentration of 3.2M in H$_2$O. Each of these preparations also contained OX063 radical (General Electric, UK) dissolved to a final concentration of 15 mM. [$^{13}$C]—/[$^{13}$C, $^{15}$N$_2$]-urea and [6-$^{13}$C]-/[6-$^{13}$C, $^{15}$N$_3$]-arginine samples were polarized in a 3.35T SpinLab Polarizer (General Electric, UK) for 1.5 hours (0.83K, 93.98 GHz), while: [5-$^{13}$C]-/[$^{13}$C, $^{15}$N]-glutamine samples were polarized in a 5T SpinLab Polarizer for 2 hours (0.83K, 93.98 GHz). Following polarization, the HP substrate was ejected from the polarizer via rapid dissolution, during which a superheated solution of 100 mM Tris 1 mM EDTA in pH 7.4 H$_2$O or pD 7.4 D$_2$O is run through the sample vial to dissolve the polarized substrate and eject it into a pre-chilled glass vial (–20° C.).

Figure 8:
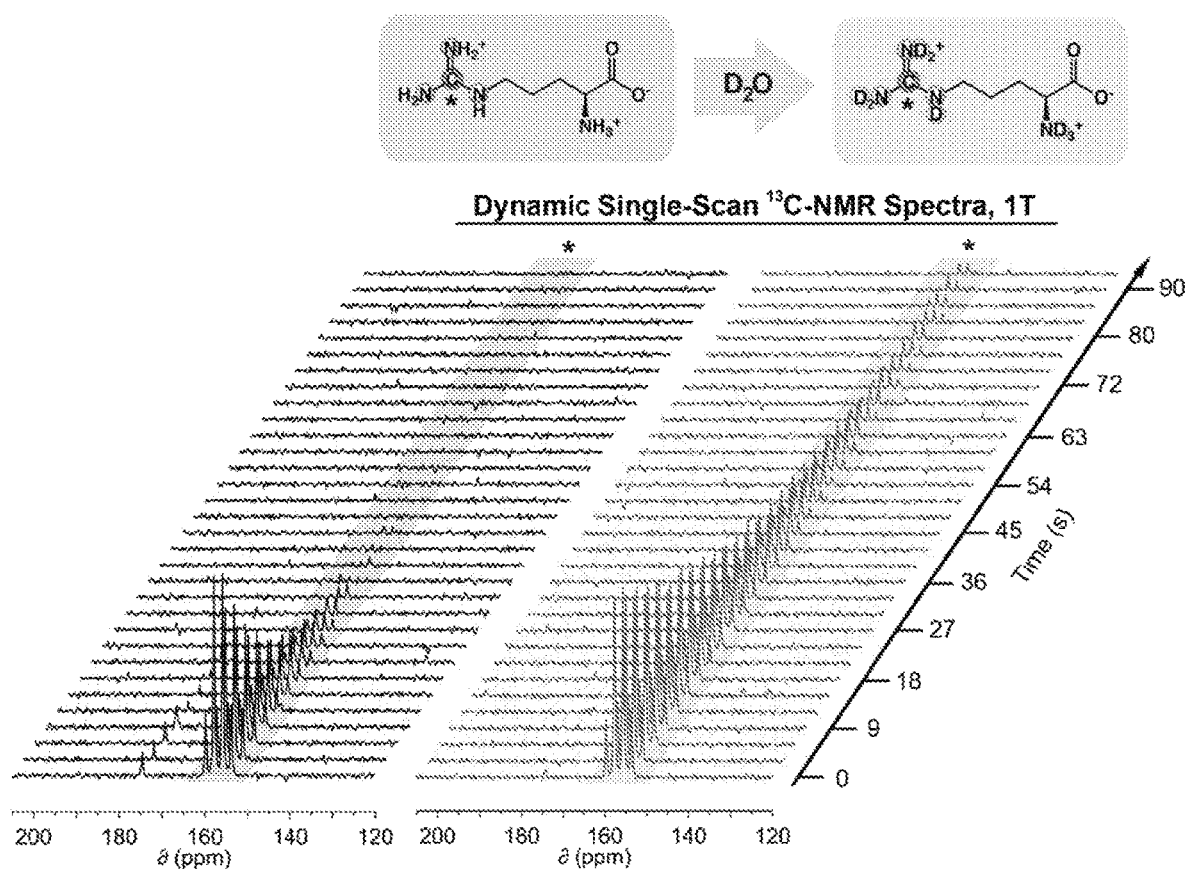
FIG. 8 shows the dynamic single-scan $^{13}C$-NMR spectra acquired in a 1T field, acquired from hyperpolarized [6-$^{13}C$, $^{15}N_3$]-Arginine dissolved in buffered $H_2O$ (left spectra) and hyperpolarized [6-$^{13}C$, $^{15}N_3$]-Arginine dissolved in buffered $D_2O$ (right spectra). Arginine carbon-6 resonance is marked with an asterisk and appears as a quartet.

As shown in FIG. 8 for [6-$^{13}$C, $^{15}$N$_3$]-arginine, dissolution of the hyperpolarized substrate in buffered D$_2$O, compared to buffered H$_2$O, resulted in prolonged hyperpolarized carbon $T_1$ values at 1T, and this phenomenon. $^{15}$N enrichment at the carbon directly bonded to nitrogen did not appear to change hyperpolarized $T_1$ values in either solvent for all compounds. However, spectra acquired from compounds without $^{15}N$ enrichment exhibited reduced SNR and line-broadening due to shortening of $T_1$ at low field, during the time immediately following dissolution and prior to transfer to 1T NMR, and shortening of $T_2$ via quadrupolar relaxation. Hyperpolarized $T_1$ values at 1T for all compounds are summarized in Table 2.

TABLE 2

| Compound | Labeling | $H_2O$ Value (s) | n | $D_2O$ Value (s) | n |
|---|---|---|---|---|---|
| Glutamine | $^{13}C$ | 21.8 ± 1.8 | 3 | 34.1 ± 2.5 | 3 |
|  | $^{13}C, ^{15}N$ | 23.6 ± 2.1 | 3 | 31.2 ± 3.8 | 3 |
| Urea | $^{13}C$ | 51.6 ± 5.44 | 6 | 123.8 ± 19.6 | 9 |
|  | $^{13}C, ^{15}N_2$ | 53.3 ± 2.6 | 6 | 115.9 ± 8.5 | 14 |
| Arginine | $^{13}C$ | — | — | 32.1 ± 4.5 | 3 |
|  | $^{13}C, ^{15}N_3$ | 13.3 ± 0.8 | 8 | 31.2 ± 6.8 | 5 |

Example 6: In Vivo Assays

In vivo assays may performed by measuring enzyme activity for hyperpolarized compounds of formula I, formula II, formula III, formula VI, and formula VII using murine model. The hyperpolarized compounds of the present technology will be injected into mice having the tumors or cancer cells as described herein in any embodiment. Imaging of cells expressing arginase-1, arginase-2, xanthine oxidase, and glutaminase may be obtained from $^{13}C$ signal detection using magnetic resonance imaging (MRI) or magnetic resonance spectroscopic imaging (MRSI), $^{15}N$ MRI or MRSI, $^{2}H$ MRI or MRSI, or $^{1}H$ MRI or MRSI.

Figure 9A:
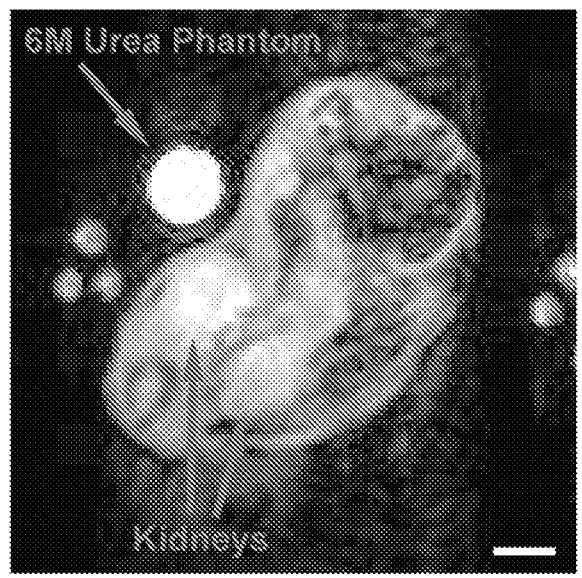
FIGS. 9A-9C show the in vivo imaging of [$^{13}C$, $^{15}N$]-urea in a mouse model.
Figure 9B:
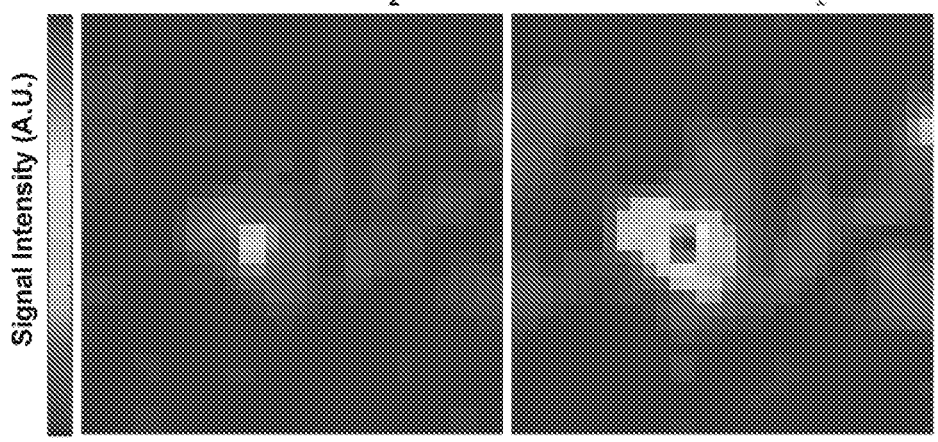
Figure 9C:
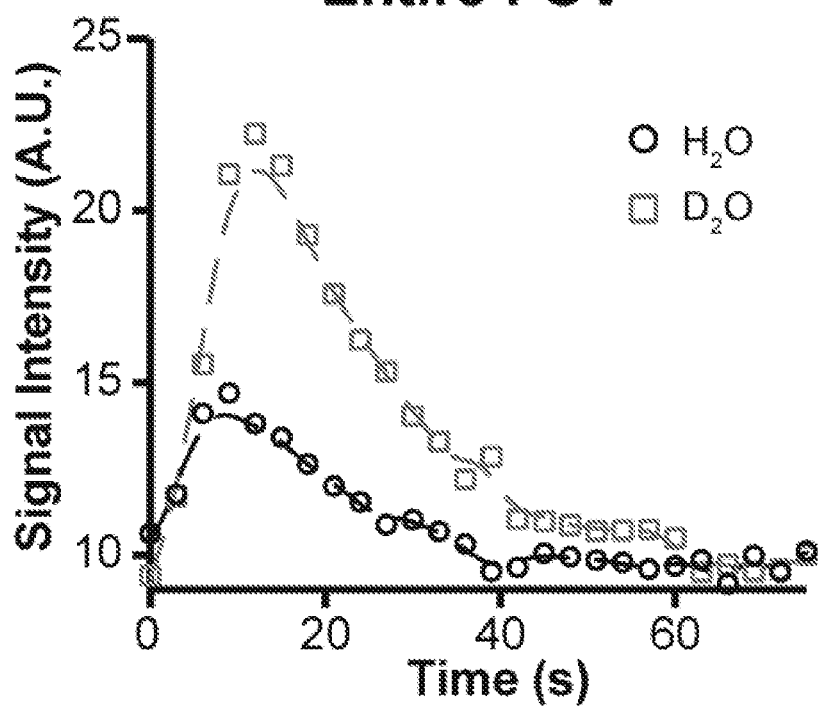

Hyperpolarized [$^{13}C$, $^{15}N_2$]-urea was studied under clinical imaging conditions. A healthy female Balb/c mouse (12 weeks old) was injected with identical volumes of hyperpolarized [$^{13}C$, $^{15}N$]-urea dissolved in either buffered $D_2O$ or $H_2O$ (FIG. 9A). Both samples were polarized for similar amounts of time and were dissolved to similar final concentrations. Immediately following the end of the injection, an axial 2D $^{13}C$ echo-planar imaging (EPI) sequence was initiated with a 3 s repetition time, 16×16 resolution with 2.25 mm×2.25 mm×10 mm voxels. FIGS. 9B and 9C demonstrate that dissolution in $D_2O$ resulted in an increased hyperpolarized signal, even after correcting for any differences in urea concentration between the two dissolutions. Following the conclusion of the imaging experiment, the mouse was removed from anesthesia and monitored for 30 minutes during which no obvious morbidity was observed as a result of the two injections. The deuterated-hyperpolarized probes of the present technology exhibited extended $T_1$ of the urea carbon resonance during QC and sample transfer, translating to higher $^{13}C$ polarization upon intravenous injection.

Example 7: Synthesis of L-glutamine (5-13C, 5-15N)

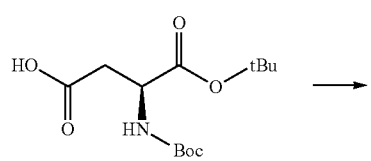

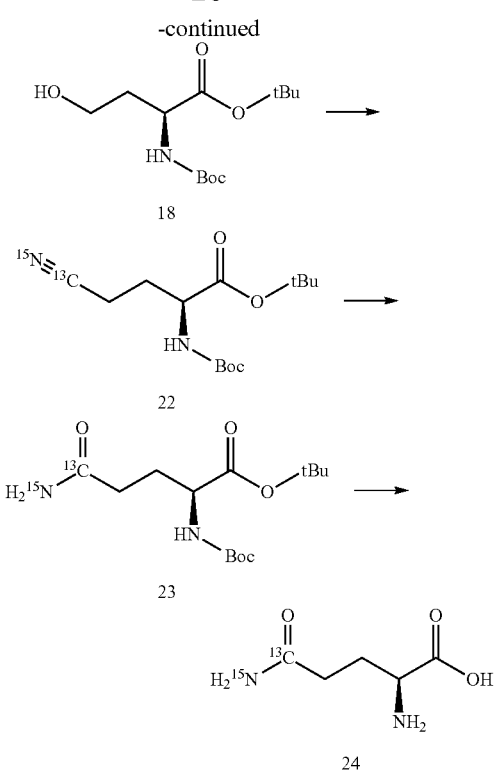

tert-butyl (tert-butoxycarbonyl)-L-homoserinate (18): An oven dried 2-neck round bottom flask was equipped with a magnetic stir bar and an argon inlet. The flask was charged with 5 g of compound 17 (17.3 mmol, 1 equiv) and sealed under an argon atmosphere. 80 mL dry THF and 1.92 g triethylamine (19.0 mmol, 1.1 equiv) were added to the flask, and the mixture was cooled in an ice-salt bath between −5 and −10° C. To this, 2.06 g ethyl chloroformate (19.0 mmol, 1.1 equiv) was added dropwise as the reaction mixture was stirred vigorously. While continuing stirring, the mixture was subsequently removed from the ice bath and allowed to equilibrate to ambient temperature over 30 minutes, after which the reaction mixture was filtered and set aside. Meanwhile a second round bottom flask was equipped with a stir bar and charged with 1.37 g sodium borohydride (36.3 mmol, 2.1 equiv) and 10 mL $H_2O$. This was cooled in an ice bath and the filtrate from the first reaction was added dropwise while stirring vigorously. After all the filtrate was added, the flask was removed from the ice bath and stirred at ambient temperature for 1 hour. The reaction mixture was washed with saturated $NaHCO_3$(1×100 mL). Organic phase was collected, and the aqueous phase was extracted with EtOAc (3×100 mL), dried with $MgSO4$, and concentrated in vacuo. Crude product was purified by flash chromatography (20:80 EtOAc:Hexanes, v/v) and dried, affording a yellow oil (18) in 83% yield (4.2 g). $^1H$ NMR (600 MHz, $CDCl_3$): δ=5.35 (d, 1H, $^3J_{H,H}$=7.2 Hz), 4.39-4.29 (1H, m), 3.73-3.58 (2H, m), 2.17-2.08 (m, 1H), 1.57-1.47 (m, 1H), 1.45 (s, 9H), 1.43 (s, 9H) ppm. $^{13}C$ NMR (151 MHz, $CDCl_3$): δ=172.1, 156.8, 82.4, 80.5, 77.4, 77.2, 77.0, 58.3, 51.0, 36.7, 28.4, 28.1 ppm. HRMS (ESI) m/z calculated for $C_{13}H_{25}NaNO_5$ (M+Na)$^+$298.1629, found 298.1630.

tert-butyl(S)-2-((tert-butoxycarbonyl)amino)-4-(cyano) butanoate (5-$^{13}C$, 5-$^{15}N$) (22): An oven dried 250 mL 2-neck round bottom flask was equipped with a magnetic stir bar and an argon inlet. The flask was charged with 1.34 g [$^{13}C$,

[15N]-KCN (20 mmol, 1.47 equiv) and 5.28 g of 18-crown-6 (20 mmol, 1.47 equiv) in 100 mL of acetonitrile and sealed under an argon atmosphere. To this, a mixture of 4.0 g compound 18 (13.6 mmol, 1.0 equiv) and 3.03 g tri-n-butylphosphine (15.0 mmol, 1.11 equiv) in 20 mL acetonitrile was added. And the mixture was cooled in methanol-ice bath to −20° C. To this mixture, 2.32 g CCl$_4$ (1.46 mL, 15.0 mmol, 1.11 equiv) was added dropwise as the reaction mixture was stirred vigorously. The flask was removed from the cold bath and stirred at ambient temperature for 24 hours. The reaction mixture was dried under reduced pressure, and 100 ml water was added and extracted with EtOAc (3×100 mL). Organic fraction was dried with MgSO$_4$, and concentrated in vacuo. Crude product was purified by flash chromatography (10:90 EtOAc:Hexanes, V/V) and dried, affording a pale-yellow solid (22) in 48% yield (1.91 g).

tert-butyl (tert-butoxycarbonyl)-L-glutaminate (5-13C, 5-15N) (23): An oven dried 50 mL single-neck round bottom flask was equipped with a magnetic stir bar and a reflux condenser. The flask was charged with 1.76 g compound 23(6.2 mmol,1 equiv), 3 mL toluene, 29 mg Wilkinson's catalyst (3.2 μmol, 0.5 mol %), 1.84 g acetaldoxime (1.9 mL, 31.2 mmol, 5 equiv). The reaction mixture is heated to reflux with an oil bath (set at 130° C.) for 24 hours and then was allowed to cool down to room temperature. The reaction mixture was dried under reduced pressure, and 20 ml water was added and extracted with EtOAc (3×20 mL), dried with MgSO$_4$, and concentrated in vacuo. Crude product was purified by flash chromatography (10:90 MeOH:DCM, V/V) and dried, affording a pale-yellow solid (23) in 92% yield (1.72 g).

(5-13C, 5-15N) L-glutamine (24): An oven dried 50 mL round bottom flask was equipped with a magnetic stir bar and charged with 1.73 g compound 23 (3.23 mmol). To this, 25 mL 1:1 trifluoroacetic acid:DCM was added and the solution was stirred at ambient temperature for 12 hours. DCM form the mixture was removed under reduced pressure, and pH was adjusted with 10% ammonia to 5. Then mixture was loaded on a prewashed column (with 5% HCl) of Dowex 50WX8-200 (H+ form, 30 g) and eluted with 1% ammonia solution. The positive fractions to ninhydrin was combined and lyophilized. White powder 650 mg was recrystallized in water-ethanol 90:10 and filtered, affording a white solid (5-$^{13}$C, 5-$^{15}$N) L-glutamine (24) in 70% yield (555 mg).

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:
1. A compound according to formulae I:

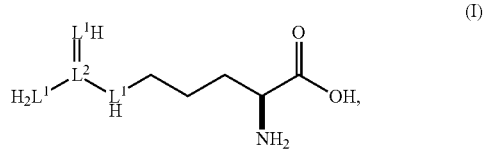

stereoisomers, tautomers, and/or pharmaceutically acceptable salts thereof;
wherein:
L$^1$ is $^{15}$N;
L$^2$ is $^{13}$C; and
▬ is a member selected from the group consisting of ⋯⋯||||| , ▬◄ and a mixture thereof.

2. The compound of claim 1, wherein 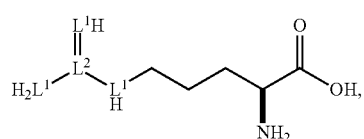 is 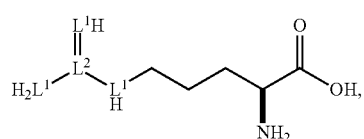.

3. A pharmaceutical composition comprising the compound of claim 1 and a pharmaceutically acceptable carrier.

4. A method of imaging comprising:
administering an effective amount of a composition comprising a hyperpolarized probe and a solvent to one or more mammalian cells;
detecting by magnetic resonance the hyperpolarized probe and/or a metabolite of the probe in the one or more mammalian cells;
wherein:
the hyperpolarized probe is a compound that has been subjected to hyper polarization and is selected from the group consisting of a compound according to formulae I, II, or III:

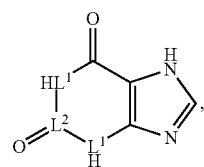

stereoisomers, tautomers, and/or pharmaceutically acceptable salts thereof;
wherein:
$L^1$ is $^{15}N$;
$L^2$ is $^{13}C$; and
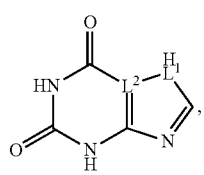 is a member selected from the group consisting of 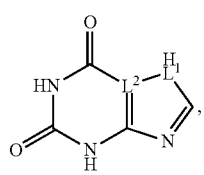, 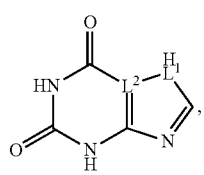, and a mixture thereof; and
the solvent comprises D2O.

5. The method of claim 4 wherein the hyperpolarized probe is the hyperpolarized compound of formula I, a stereoisomer thereof, and/or a tautomer thereof, and/or a pharmaceutically acceptable salt thereof, and the metabolite is produced by arginase.

6. The method of claim 4 wherein the one or more mammalian cells comprise a tumor associated macrophage.

7. The method of claim 4 wherein the hyperpolarized probe is the hyperpolarized compound of formula II or formula III and/or the tautomer thereof, and/or the pharmaceutically acceptable salt of any of the preceding compounds, and the metabolite is produced by xanthine oxidase.

8. The method of claim 4 wherein the one or more mammalian cells comprise one or more cancer cells.

9. The method of claim 8 wherein the one or more cancer cells are selected from one or more renal, sarcoma, lung, prostate, breast, pancreatic, oral, or epithelial cancer cells.

10. The method of claim 4, wherein the composition is administered to a mammal.

11. The method of claim 10, wherein the mammal is a human.

12. A method of imaging comprising:
contacting one or more mammalian cells with an effective amount of a composition comprising a deuterium exchanged-hyperpolarized probe and a solvent; and
detecting by magnetic resonance the deuterium exchanged-hyperpolarized probe and/or a metabolite of the probe in the one or more mammalian cells;
wherein:
the deuterium exchanged-hyperpolarized probe is a deuterated compound of formula I:

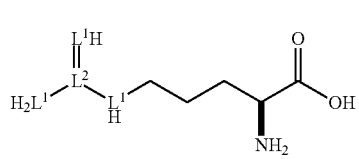

stereoisomers, tautomers, and/or pharmaceutically acceptable salts thereof;
the deuterated compound has been subjected to hyper polarization; and
the solvent comprises D2O.

13. The method of claim 12, wherein the deuterated compound exhibits a longer $T_1$ and $T_2$ relaxation time for $^{13}C$ as measured by $^{13}C$-NMR.

14. The method of claim 12, wherein the deuterium exchanged-hyperpolarized probe is the deuterated hyperpolarized compound of formula I, a stereoisomer thereof, and/or a tautomer thereof, and/or a pharmaceutically acceptable salt thereof, and the metabolite is produced by arginase.

15. The method of claim 12, wherein the one or more mammalian cells comprise a tumor associated macrophage.

16. The method of claim 12, wherein the composition is administered to a mammal.

17. The method of claim 16, wherein the mammal is a human.

18. A deuterium exchanged-hyperpolarized probe comprising a compound of formula VI:

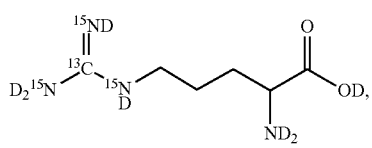

stereoisomers, tautomers, and/or pharmaceutically acceptable salts thereof.

19. A composition comprising a solvent and a hyperpolarized probe according to formulae I, II, III, and/or VI:

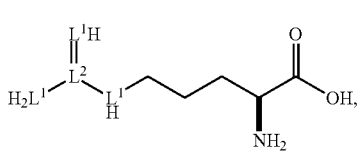

(II)
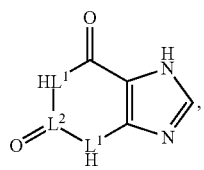
(III)
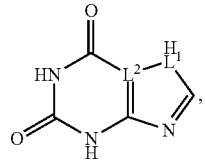
(VI)
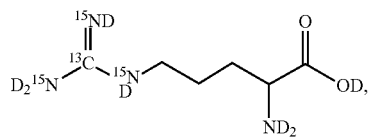
stereoisomers, tautomers, and/or pharmaceutically acceptable salts thereof;
wherein:
$L^1$ is $^{15}N$;
$L^2$ is $^{13}C$;
▬ is a member selected from the group consisting of ⋯⋯⫼⫼⫼ , ◂▬ , and a mixture thereof; and
the solvent comprises D2O.
* * * * *